(12) United States Patent
Bezwada

(10) Patent No.: US 7,858,077 B2
(45) Date of Patent: Dec. 28, 2010

(54) FUNCTIONALIZED PHENOLIC ESTERS AND AMIDES AND POLYMERS THEREFROM

(75) Inventor: Rao S. Bezwada, Whitehouse Station, NJ (US)

(73) Assignee: Bezwada Biomedical LLC, Hillsborough, NJ (US)

( * ) Notice: Subject to any disclaimer, the term of this patent is extended or adjusted under 35 U.S.C. 154(b) by 1453 days.

(21) Appl. No.: 11/220,044

(22) Filed: Sep. 6, 2005

(65) Prior Publication Data

US 2006/0173065 A1 Aug. 3, 2006

Related U.S. Application Data

(60) Provisional application No. 60/647,996, filed on Jan. 28, 2005.

(51) Int. Cl.
*A61K 31/74* (2006.01)
(52) U.S. Cl. .................................................. 424/78.08
(58) Field of Classification Search ........................ None
See application file for complete search history.

(56) References Cited

U.S. PATENT DOCUMENTS

| | | | |
|---|---|---|---|
| 4,130,639 A | 12/1978 | Shalaby |
| 4,532,928 A | 8/1985 | Bezwada |
| 4,605,730 A | 8/1986 | Shalaby |
| 4,653,497 A | 3/1987 | Bezwada |
| 4,689,424 A | 8/1987 | Shalaby |
| 4,886,570 A | 12/1989 | Davis |
| 5,082,925 A | 1/1992 | Shalaby |
| 5,759,830 A | 6/1998 | Vacanti |
| 5,859,150 A | 1/1999 | Jamiolkowski |
| 5,951,997 A | 9/1999 | Bezwada |
| 6,468,519 B1 | 10/2002 | Uhrich |
| 6,689,350 B2 | 2/2004 | Uhrich |
| 6,773,721 B1 | 8/2004 | Wong |
| 6,861,068 B2 | 3/2005 | Ng |
| 6,869,615 B2 | 3/2005 | Chen |
| 6,890,561 B1 | 5/2005 | Blatt |
| 2002/0169275 A1 | 11/2002 | Matsuda |
| 2003/0216307 A1 | 11/2003 | Kohn |
| 2003/0232091 A1 | 12/2003 | Shefer |
| 2004/0117007 A1 | 6/2004 | Whitbourne |
| 2005/0074493 A1 | 4/2005 | Mehta |
| 2005/0095300 A1 | 5/2005 | Wynn |
| 2005/0112171 A1 | 5/2005 | Tang |
| 2005/0152958 A1 | 7/2005 | Cordes |

FOREIGN PATENT DOCUMENTS

WO WO 2004089420 A1 * 10/2004

OTHER PUBLICATIONS

Mukaiyama, tetrahedron 55, 1999, 8609-8670.*
Estrina, G. A., Catalytic interaction between e-caprolactone and diols, Polymer Science USSR 11(5)1132:1135(1989).
Yasukawa, T.,Drug delivery systems for vitreoretinal diseases, Progress in Retinal and Eye Research 23:253:281(2004).
Frank, A., Controlled release from bioerodible polymers: effect of drug type and polymer composition, Journal of Controlled Release 102:333:344(2005).
Ould-Ouali, L., Self-assembling PEG-p(CL-co-TMC) copolymers for oral delivery of poorly water-soluble drugs . . . Journal of Controlled Release 102: 657-668(2005).

* cited by examiner

*Primary Examiner*—Michael G Hartley
*Assistant Examiner*—Paul Dickinson
(74) *Attorney, Agent, or Firm*—Fox Rothschild LLP; Peter J. Butch, III; Shahnam Sharareh

(57) ABSTRACT

The present invention relates to a compound of the formula:

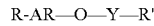

Wherein R represents one or more members selected from H, alkoxy, benzyloxy, aldehyde, halogen, carboxylic acid, $-NO_2$, $-NH_2$, $-NHCOCH_3$, and $-NH-Y-R'$, which is attached directly to AR or attached through an aliphatic chain. The carboxylic acid moiety in R includes but is not limited to the following carboxylic acids: benzoic acids, cinnamic acids, ferulic acid, caffeic acid, syringic acid, salicylic acid, vanillic acid, phenylacetic acids, phenylpropionic acids, and sinapinic acid.
-AR—O— is a biologically active phenolic moiety comprising 1 to 6 substituted or unsubstituted aryl rings that are directly bonded to each other, fused together, or joined through a linking group.
Y represents a member selected from:
—$COCH_2O$— (glycolic ester moiety)
—$COCH(CH_3)O$— (lactic ester moiety)
—$COCH_2OCH_2CH_2O$— (dioxanone ester moiety)
—$COCH_2CH_2CH_2CH_2CH_2O$— (caprolactone ester moiety)
—$CO(CH_2)_mO$— where m is an integer between 2-4 and 6-24 inclusive
—$COCH_2O(CH_2CH_2O)_n$— where n is an integer between 2 and 24, inclusive; and
R' is either hydrogen or a benzyl or an alkyl group, the alkyl group being either straight-chained or branched.

The resultant functionalized phenolic compounds, used singly or in combinations, and their polymers have controllable degradation profiles, releasing the active component over a desired time range. The polymers are useful for biomaterials and biomedical devices, wherein said biologically active phenolic moiety is a residue of a phenolic compound.

22 Claims, No Drawings

FUNCTIONALIZED PHENOLIC ESTERS AND AMIDES AND POLYMERS THEREFROM

CROSS-REFERENCE TO RELATED APPLICATIONS

This application claims the benefit of U.S. Provisional Patent Application Ser. No. US60/647,996 entitled "Functionalized Phenolic Compounds and Polymers Therefrom" filed Jan. 28, 2005. The disclosures of this provisional patent application are incorporated herein by reference in their entireties.

STATEMENT REGARDING FEDERALLY SPONSORED RESEARCH OR DEVELOPMENT

Not applicable.

FIELD OF THE INVENTION

The present invention relates to the discovery of functionalized phenolic compounds, functionalized phenolics containing amine and/or carboxylic acid groups, and their polymers. The resultant functionalized phenolic compounds and their polymers have controllable degradation profiles, releasing the active phenolic component over a desired time range. They can be used in combination in order to extend the time range over which the active ingredient is released. The compounds can also be used in combination with the compounds of U.S. Provisional Patent Application Ser. No. US60/647, 996 to further increase their usefulness by providing still greater variation in, and control of, the degradation or hydrolysis range of the compounds in the mixture.

BACKGROUND OF THE INVENTION

The terms phenolic and phenolic compound in the context of the present invention are defined chemically as a substance which has one or more aromatic rings and bears one or more hydroxyl substituents on the ring, including functional derivatives such as esters, methyl ethers, glycosides and other derivatives that are apparent to those skilled in the art. Phenol (hydroxybenzene) is the simplest example of a phenolic compound, but most phenolic compounds have two or more hydroxyl groups and are bioactive substances occurring widely in food plants that are eaten regularly by substantial numbers of animals and people and have been found to be safe compounds. Included in the definition of phenolics are polyphenols having complex substitution patterns, compounds having condensed rings, and phenolics containing one or more amine moieties and/or carboxylic acid moieties.

An example of a phenolic compound containing an amine moiety is p-aminophenol, the intermediate for paracetamol. An example of a phenolic compound containing both an amine and a carboxylic acid group is p-amino salicylic acid.

Phenolic and polyphenolic compounds are found widely in nature: in cereals, legumes, nuts, oilseeds, plant oils, fruits, vegetables, tea, coffee, cocoa, beer, wine, herbal products, such as Echinacea, ginseng, gingko biloba, St. John's wort, valerian, hawthorne, ginger, licorice, milk thistle, goldenseal, devil's claw, black cohosh, saw palmetto, and kava kava, for example. These substances are essential for growth and reproduction of plants and serve as antifeedants and antipathogens, among other purposes. Phenolic compounds aid in the maintenance of food, fresh flavor, taste, color and prevention of oxidation deterioration. In particular, many phenolic compounds are attracting the attention of food and medical scientists because of their antioxidative, anti-inflammatory, antimutagenic, and anticarcinogenic properties and their capacity to modulate key cellular enzyme functions. Phenolic pigment plant products and function as antibiotics, natural pesticides, signal substances for the establishment of symbiosis with rhizobia, attractants for pollinators, protective agents against ultraviolet light, insulating materials to make cell walls impermeable to gas and water and as structural materials to give plants stability. The members of this class have many valuable uses in the fields of nutrition, nutriceuticals, pharmaceuticals, medicine, agricultural chemistry and in other fields of technology.

Examples of naturally occurring phenolic compounds include, but are not limited to: bergaptol, caffeic acid, capsaicin, coumarin, daidzein, 2,5-dihydroxybenzoic acid, ferulic acid, flavonoids, glycitein (isoflavone), 4-hydroxycinnamic acid, 4-hydroxycoumarin, isopimpinellin, resveratrol, synapic acid, vanillic acid, vanillin, and the derivatives of all of the above.

Vanillin is a single-ring phenolic compound derived from the breakdown of lignin, a complex phenolic polymer that gives seasoned wood its color, hardness and mass. Natural vanilla flavoring comes from vanillin plus several other aromatic compounds in the seed capsules of the vanilla orchid. It is used as a flavoring agent in foods, beverages, confectionery, and pharmaceuticals. It is also used in perfumery.

Coumarin is a double-ring phenolic compound that imparts the distinctive sweet smell to newly mown hay. Coumarin is also an anticoagulant that represses the synthesis of prothrombin, a plasma protein produced in the liver in the presence of vitamin K. Prothrombin is the precurser of the enzyme thrombin, which catalyzes the conversion of fibrinogen to fibrin in the clotting process. Threads of fibrin wind around blood platelets in the damaged area of a blood vessel and provide a framework of a blood clot. Coumarin is converted into the anticoagulant dicoumarin during the improper curing of sweet clover hay. Aminocoumarins, such as novobiocin, clorobiocin and coumermycin A1, serve, among other uses, as antibiotics. Furanocoumarins, found in citrus fruits, celery, parsley, and parsnips, include the useful compounds psoralen, bergapten, xanthotoxin, isopimpinellin and 4,5',8-trimethylenepsoralen. Isopimpinellin has been shown to block DNA adduct formation and skin tumor initiation in mice.

Flavonoids, sometimes called bioflavonoids, are 3-ring phenolic compounds consisting of a double ring attached by a single bond to a third ring. Examples include flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, and leucoanthocyanins. In leaves they block far ultraviolet light (which is highly destructive to nucleic acids and proteins), while selectively admitting light of blue and red wavelengths that is crucial for photosynthesis. Flavonoids include the water-soluble pigments, such as anthocyanins, that are found in cell vacuoles. Water-soluble flavonoids are responsible for the color of many flowers and can range from red to blue. Flavonols are colorless or yellow flavonoids found in leaves and many flowers. Some nutritionists recommend flavonoids (bioflavonoids and isoflavones) in order to maintain healthy tissues and promote the proper balance of hormones and antioxidants in the body. They may be obtained as supplements and from a good diet of fruits, vegetables and soy protein. Flavonoids possess the following important properties: anti-inflammatory, by inhibiting histamines, prostaglandins, and enzymes involved in the inflammatory response; anti-allergic, by inhibiting histamine production; anticarcinogenic, due to its antioxidant activity. As an antioxidant the flavonoids are more powerful free radical scavengers than Vitamin C and E.

A high bioflavonoid intake, according to the literature, is related to a lower risk of heart attack. Bioflavonoids have been shown to improve the integrity of small veins and capillaries, thus decreasing their permeability and fragility. A therapeutic dose of bioflavonoids is helpful for conditions related to chronic venous insufficiency (CVI). Some examples are: thrombophlebitis, thrombosis, varicose veins, leg ulcers, spider veins, hemorrhoids, chronic nosebleeds, prolonged menstrual bleeding. Even eye problems like macular degeneration and diabetic retinopathy have been helped with bioflavonoids. Bioflavonoids inhibit the destruction of collagen and actually support repair by cross-linking collagen fibers and reinforcing the connective tissue matrix. This means that, along with the anti-inflammatory effects, bioflavonoids can be very helpful for tendonitis, arthritis, rheumatoid arthritis, joint injury, fibromyalgia, cellulite, and gout. Bioflavonoids do not interact with most drugs.

Isoflavones exert a broad spectrum of biological activities. Besides antioxidant and estrogenic activities, isoflavones protect against several chronic diseases. Results of epidemiological studies indicate that consumption of soybean isoflavones lowers the incidence of breast, prostate, urinary tract and colon cancers. They also provide protection against coronary heart diseases and osteoporosis. Some examples of important isoflavones are isoflavone, daidzein, prunetin, biochanin A, orobol, santal, pratensein, formononetin, genistein, glycitein, and the glucosides, β-glycosides and other derivatives of the aforementioned isoflavones. This list is not meant to be all-inclusive.

Resveratrol, discovered in the grape skins of the grapes used to produce red wines, has been shown to lower the risk for coronary heart disease by inhibiting the plaque build-up or clogging of arteries by increasing the level of high density lipoproteins (HDLs) in the blood. Beneficial HDLs carry cholesterol away from the arteries so that it doesn't form plaque deposits in the arterial walls. Resveratrol also reduces blood platelet aggregation or clotting (thrombosis) within the blood vessels. Resveratrol belongs to the class of plant chemicals called phytoalexin. Plants use them as a defense mechanism in response to attacks by fungi and insects. One interesting phytoalexin called psolaren, having a chemical structure similar to coumarin, has been used in the treatment of certain cancers, including T-cell lymphomas in AIDS patients.

Bioflavonoids, specifically proanthcyanidins, are found in grape seed extract. The proanthcyanidins appear to enhance the activity of vitiamin C. Vitamin C protects the cells from the damaging oxidation of free radicals, thus preventing mutations and tumor formation. The bioflavonoids in grape seed extract may also reduce the painful inflammation of swollen joints and prevent the oxidation of cholesterol in arteries that leads to plaque in the arterial walls.

Capsaicin is the active component of cayenne pepper. The capsaicins are amides of vanillylamine and $C_8$ and $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4× daily may help peripheral neuropathic pain, post-herpetic neuralgia, trigeminal neuralgia, psoriasis and fibromyalgia. It is also useful for diabetic neuropathy, cluster headaches, earache, osteo- and rheumatoid arthritis. Capsaicin is a powerful pain reliever.

Sinapinic acid (sinapic acid) and its esterified forms are the predominant phenolic acid compounds found in rapeseed, contributing to its flavor and aroma. The sinapinic acid compounds have been shown to exhibit an anti-inflammatory action and have antimicrobial properties.

Hydrocinnamic acids are the tea polyphenols, examples of which are chlorogenic acid, caffeic acid and ferulic acid. They have been shown to block the nitrosation of amines by reducing nitrate to nitric acid or by forming C-nitroso compounds, thus blocking hepatotoxicity, lowering the risk of breast cancer metastasis—green tea egcg (epigallocatechin-3-gallate).

Naproxen, paracetanol, acetaminophen and acetylsalicylic acid are phenolics that belong to the class of drugs called non-steroidal anti-inflammatory drugs or NSAIDs. The NSAIDs provide relief by blocking the action of prostaglandins, which are hormone-like substances that contribute to pain, inflammation, fever and muscle cramps.

Synthetic and naturally-occuring phenolic moieties, some of which may contain amine groups, carboxylic acid groups, or aminoacids, are part of many drugs. Examples of these medicinals include acenocoumarol, acetarsol, actinoquinol, adrenalone, alibendol, aminosalicylic acids, amodiaquine, anethole, balsalazide, bamethan, benserazide, bentiromide, benzarone, benzquinamide, bevantolol, bifluranol, buclosamide, bupheniode, chlorobiocin, chlorotrianisene, chloroxylenol, cianidanol, cinepazide, cinitapride, cinepazide, cinmetacin, clebopride, clemastine, clioquinol, coumermycin A1, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indometacin, ipriflavone, isoetarine, isoprenaline, isoxsuprine, itopride hydrochloride, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, novobiocin, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Additional bioactive phenolic compounds include acacetin, 4-acetamido-2-methyl-1-naphthol, acetaminophen, albuterol, allenolic acid, aloe emodin, aloin, β-amino-4-hydroxy-3,5-diiodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol A, bisphenol B, butylated hydroxyanisole, butylated hydroxytoluene, capobenic acid, trans-1-(3'-carboxy-4'-hydroxyphenyl)-2-(2'',5''-dihydroxyphenyl)ethane, catechin, chlorogenic acid, m-chlorophenol, 5-chloro-8-quinolinol, chloroxyphenol, chloroquinaldol, chromonar, chrysin, cinametic acid, clorophene, coniferyl alcohol, p-coumaric acid, coumarin-3-carboxylic acids, coumarin-8-carboxylic acids, coumestrol, coumetarol, daphnetin, datiscetin, deoxyepinephrine, 3,5-diiodothyronine, 3,5-diiodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophenone, gallic acid, gardenins, genistein, gentisyl alcohol, gepefrine, geranylhydroquinone, [6]-gingerol, gossypol, guaiacol, guaifenesin, harmalol, hematoxylin, hinderin, homoeriodictyol, homogentisic acid, homovanillic acid, hydroxyamphetamine, 2-hyroxy-5-(2,5-dihydroxybenzylamino)-2-hydroxybenzoic acid, 4-hydroxy-3-methoxymandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 7-methoxycoumarin-3-carboxylic acid, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxyphenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl) methylenepropanedinitrile, thymol, thyropropic acid, thyroxine, tiratricol, tyrosine, vanillic acid, and vanillin.

Reactions of phenolics with bioabsorbable polymers have been reported in Shalaby U.S. Pat. No. 5,082,925 and Matsuda US 20020169275. Reactions of bioactive compounds with bioabsorbable polymers have been reported, for example in Uhrich U.S. Pat. No. 6,468,519, Uhrich U.S. Pat. No. 6,689,350, and Kohn US20030216307.

Various types of controlled release technologies, some of which may be suitable for use with phenolic compounds have been reported in the literature. Examples are Yasukawa (2004), Blatt U.S. Pat. No. 6,890,561, Ould-Ouali (2005), Frank (2005), Chen U.S. Pat. No. 6,869,615, Cordes US 20050152958, Wynn US 20050095300, Mehta US 20050074493, Ng U.S. Pat. No. 6,861,068, Wong U.S. Pat. No. 6,773,721, Whitborne US 20040117007, and Shefer US 20030232091.

An article by G. A. Estrine (1989) speaks to the catalytic reaction of epsilon-caprolactone with diols to form an intermediate complex.

Uses of bioabsorbable polymers in the biomedical field have been reported, for example, in the following patents: Shalaby U.S. Pat. No. 4,130,639, Bezwada U.S. Pat. No. 4,532,928, Langer U.S. Pat. No. 4,886,870, Shalaby U.S. Pat. No. 4,605,730, Bezwada U.S. Pat. No. 4,653,497, Shalaby U.S. Pat. No. 4,689,424, Vacanti U.S. Pat. No. 5,759,830, Jamiolkowski U.S. Pat. No. 5,895,150, Bezwada U.S. Pat. No. 5,951,997, and Yiewen US 20050112171.

While phenolic compounds have various known beneficial uses, they generally are insoluble or partially soluble in water or the human body and are difficult to hydrolyze. They are also very difficult to polymerize in the phenolic state. It is desirable to do so and to be able to control their rate of action, target release into specific organs, extend release over a prolonged period of time and/or to delay or sustain their efficacy. The claimed invention corrects these drawbacks.

BRIEF SUMMARY OF THE INVENTION

The present invention provides biologically active functionalized phenolic compounds. Accordingly, a first aspect of the invention provides a compound of the formula:

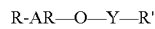

R—AR—O—Y—R'

Wherein R represents one or more members selected from the group consisting of H, alkoxy, benzyloxy, aldehyde, halogen, carboxylic acid, —$NO_2$, —$NH_2$, —NH-$COCH_3$, and —NH—Y—R', which is attached directly to AR or attached through an aliphatic chain. The carboxylic acid moiety in R includes but is not limited to the following carboxylic acids: benzoic acids, cinnamic acids, ferulic acid, caffeic acid, syringic acid, salicylic acid, vanillic acid, phenylacetic acids, phenylpropionic acids, sinapinic acid;

-AR—O— is a biologically active phenolic moiety comprising 1 to 6 substituted or unsubstituted aryl rings that are directly bonded to each other, fused together, or joined through a linking group;

Y represents a member selected from:
—$COCH_2O$— (glycolic ester moiety)
—$COCH(CH_3)O$— (lactic ester moiety)
—$COCH_2OCH_2CH_2O$— (dioxanone ester moiety)
—$COCH_2CH_2CH_2CH_2CH_2O$— (caprolactone ester moiety)
—$CO(CH_2)_mO$— where m is an integer between 2-4 and 6-24 inclusive
—$COCH_2O(CH_2CH_2O)_n$— where n is an integer between 2 and 24, inclusive; and R' is either hydrogen or a benzyl or an alkyl group, the alkyl group being either straight-chained or branched.

The functionalized compounds of the formula can alter the native value or efficacy of the pre-functionalized phenolic compound by modifying and controlling the onset of biodegradation, targeting the organ in which to release the phenolic compound and/or regulate the length of action of the phenolic compound thereof.

Another aspect of this invention involves functionalizing a phenolic compound with one or more moieties, such as a glycolic ester moiety, lactic ester moiety, p-dioxanone ester moiety, ε-caprolactone ester moiety, —$CO(CH_2)_mO$—, where m is one of the integers 2, 3, 4 and between 6 and 24 inclusive, and —$COCH_2O(CH_2CH_2O)_n$— where n is an integer between 2 and 24, inclusive, to form a new chemical entity. The resultant functionalized phenolic compound is hydrolyzable and biodegradable, providing controlled release of the active phenolic component over a time period of from several weeks to four years, depending on the functionalized moiety or combination of moieties selected for the reaction.

In a further aspect of the invention one can blend compounds comprising one or more of the functionalization species with one or more species of phenolic moieties.

A still further aspect of the invention is to create polymers from the functionalized phenolic compounds of this invention that are difunctional, that is those species having more than one hydroxyl group. Polymers of the functionalized phenolic compounds also have specific ranges over which they release the active phenolic moiety. One can blend polymers made from functionalized phenolics derived from one or more of the functionalization species and one or more species of phenolic moieties to obtain the release range desired for the specific application into the body of a mammalian, including a human, or the environment. This release range varies with the species used for functionalization. The combinations or blends of these entities may comprise an amount of from 0.5% to 99.5% of each species.

The functionalized compounds have potential application in the same or similar areas as the non-functionalized phenolic compounds, since the compounds retain the innate properties of the active phenolic compound. For example, they serve as enhanced drugs, cancer preventing agents, nutrition supplements, nutriceuticals, antioxidants, controlled release preparations, cosmetic applications, food stuffs, flavors, coatings, drug intermediates, solvents for drugs, new monomers for polymerization. When polymerized, the polymers are useful for biomedical devices, including absorbable implantable devices, surgical sutures, drugs, nutrition supplements, biodegradable chewing gum, nutriceuticals, drug delivery, cosmetic applications, flavors, and coatings, including coatings for medical devices such as stents. This list of uses is provided as example and is not meant to be all-inclusive. In addition, the active portion of the functionalized phenolic has improved bioavailability, increased solubility, and better control of the degradation to provide a targeted delivery of the active phenolic component. The compounds can be further reacted and sometimes further polymerized, thus increasing their usefulness.

DETAILED DESCRIPTION OF THE INVENTION

The functionalization of phenolic compounds, including those containing one or more amine groups, carboxylic acid groups and amino acids, produces a hydrolysable, bioabsorbable compound. This process enhances the native value of the phenolic compound by providing the resultant compound or combination of compounds with a specific, controlled degradation profile or range, enabling the controlled release of the phenolic compound over an extended, controllable time range. The different controlled release profiles represent slow, moderate and/or rapid release of the active substance (phenolic) or substances (phenolics). This release may be targeted to one or more specific organs or parts of the body. This invention greatly extends the usefulness of phenolic compounds and provides greater control of the bioavailability of the phenolics while retaining the inherent biological properties of the phenolic compound. An additional benefit of some of the compounds of this invention is that the active substance or phenolic compound released is the same substance as the starting phenolic material.

Those functionalized phenolics derived from difunctional phenolic compounds can be readily polymerized into absorbable or biodegradable polymers. The functionalized phenolics containing at least two hydroxyl groups will combine with a substance containing two carboxyl groups to form a polyester. Those containing a hydroxyl group and a carboxylic acid group will self-condense to form a polyester. Those containing a hydroxyl group and an amine group will react with a carboxylic acid to form a polyester amide. Those functionalized phenolics that are diamines will react with a carboxylic acid to form a polyamide. These biodegradable polymers from functionalized phenolics can be prepared with controlled degradation profiles and are suitable for the targeted delivery of active phenolic components, including biomedical applications, such as absorbable medical devices, surgical sutures, and stent coatings.

The compounds described in this patent can be used singly or in combination, that is, one or more phenolic compounds can be reacted with one or more of the functionalization moieties, thus providing a means of increasing the time range over which the active phenolic compound is released. The species or combination of species can be used in combination with the compounds of U.S. Provisional Patent Application Ser. No. US60/647,996 to further increase usefulness by providing still greater variability and control of the degradation range of the compounds in the mixture. The compounds of the present invention which are difunctional can be polymerized with one or more compounds taken from the group consisting of:

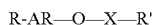

R-AR—O—X—R'

Wherein R represents one or more members selected from the group consisting of H, alkoxy, benzyloxy, aldehyde, halogen, carboxylic acid, —NO$_2$, —NH$_2$, —NHCOCH$_3$, and —NHCOCH$_2$OH, which is attached directly to AR;

-AR—O— is a biologically active phenolic moiety comprising 1 to 6 substituted or unsubstituted aryl rings that are directly bonded to each other, fused together, or joined through a linking group;

X represents a member selected from:
—CH$_2$COO— (glycolic acid moiety)
—CH(CH$_3$)COO— (lactic acid moiety)
—CH$_2$CH$_2$OCH$_2$COO— (dioxanone moiety)
—CH$_2$CH$_2$CH$_2$CH$_2$CH$_2$COO— (caprolactone moiety)
—(CH$_2$)$_y$COO— where y is one of the numbers 2, 3, 4 and 6-24 inclusive
—(CH$_2$CH$_2$O)$_z$CH$_2$COO— where z is an integer between 2 and 24, inclusive; and R' is either hydrogen or a benzyl or an alkyl group, the alkyl group being either straight-chained or branched.

Examples of biologically active phenolic residues represented by -AR—O include, but are not limited to, phenols, naphthols, flavonoids, isoflavonoids, coumarins, chromones, chalcones, cinnamic acids, simple benzoic acids, indoles, acetophenones, benzophenones, alkaloids, catechins, catechols, hydrocinnamic acids, phenolic acids, resorcinol, hydroquinone, drugs containing phenolic groups, natural products containing phenolic groups, amino acids containing phenolic groups, and drugs containing naphthols.

The present invention provides biologically active functionalized phenolic compounds. Accordingly, a first aspect of the invention provides a compound of the formula:

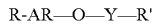

R-AR—O—Y—R'

Wherein R represents one or more members selected from the group consisting of H, alkoxy, benzyloxy, aldehyde, halogen, carboxylic acid, —NO$_2$, —NH$_2$, —NHCOCH$_3$, and —NH—Y—R', which is attached directly to AR or attached through an aliphatic chain. The carboxylic acid moiety in R includes but is not limited to the following carboxylic acids: benzoic acids, cinnamic acids, ferulic acid, caffeic acid, syringic acid, salicylic acid, vanillic acid, phenylacetic acids, phenylpropionic acids, and sinapinic acid;

-AR—O— is a biologically active phenolic moiety comprising 1 to 6 substituted or unsubstituted aryl rings that are directly bonded to each other, fused together, or joined through a linking group;

Y represents a member selected from:
—$COCH_2O$— (glycolic ester moiety)
—$COCH(CH_3)O$— (lactic ester moiety)
—$COCH_2OCH_2CH_2O$— (dioxanone ester moiety)
—$COCH_2CH_2CH_2CH_2CH_2O$— (caprolactone ester moiety)
—$CO(CH_2)_mO$— where m is an integer between 2-4 and 6-24 inclusive
—$COCH_2O(CH_2CH_2O)_n$— where n is an integer between 2 and 24, inclusive; and R' is either hydrogen or a benzyl or an alkyl group, the alkyl group being either straight-chained or branched.

Incorporated as phenolics forming the embodiments of this invention are all biologically active phenolic compounds mentioned in this document, especially those containing amine groups, carboxylic acid groups and amino acid moieties and all phenolic compounds contained in the following texts:

Shahidi, Ferriodoon and Marian Naczk, *Phenolics in Food and Nutriceuticals*, Boca Raton, Fla.: CRC Press, 2003.

Kleemann, A. et al, *Pharmaceutical Substances*, 4th Edition, New York: Thieme (2000).

*Phenolic Compounds in Food and Their Effects on Health II; Antioxidants and Cancer Prevention*, ACS Symposium Series No. 507, Washington, D.C.: ACS, 1992.

*Food Phytochemicals for Cancer Prevention I*, ACS Symposium Series N. 546, Washington, D.C.: ACS, 1994.

*ROMPP Encyclopedia Natural Products*, New York: Thieme, 2000.

*The Merck Index*, 12$^{th}$ edition, Rahway, N.J.: Merck and Company, 1996.

*A Single Source for Flavonoids and Coumarins* (2005-2006), INDOFINE Chemical Company, Inc.

All information regarding biologically active phenolics contained in these books is incorporated into this patent by reference.

It is understood that the phenolic starting material for the compounds of this invention may be a phenolic compound or may be a precursor to a phenolic, such as a methoxyphenol, benzyloxyphenol, acetoxyphenol and the like, and also phenolics containing amine groups and/or carboxylic acid groups which are attached directly to AR or attached through an aliphatic chain.

The phenolic compounds may be monofunctional, that is, containing one hydroxyl group, difunctional, containing two hydroxyl groups, or polyfunctional, containing from 3 to 25 hydroxyl groups, inclusive. All hydroxyl groups may be reacted in the synthesis of the functionalized phenolic compounds of this invention.

Functionalization Moieties

Glycolic acid and lactic acid are also known as alpha hydroxy acids (AHA) and are present in fruits and other foods. These acids are helpful in treating a variety of skin ailments, such as dry skin, acne, and sunspots. These acids also improve skin texture and lessen fine facial wrinkles. Both glycolic and lactic acids also help loosen and remove dead skin cells. These acids are present in many of the healthiest foods we eat and drink, and they are considered to be safe when used correctly.

Glycolic acid occurs naturally as the chief acidic constituent of sugar cane juice and occurs in beet juice and unripe grapes. Its formula is $HOCH_2COOH$ and it is biodegradable. When glycolic acid is heated it readily loses water by self-esterification to form polyglycolic acid.

Glycolic acid can function as both an acid and an alcohol. This dual functionality leads to a variety of chemical reactions and valuable physical properties. Many surgical devices, including implantable devices, are made from polyglycolic acid. Studies of cosmetic applications have found that glycolic acid at low concentrations will diminish the appearance of fine lines on the skin.

The process of preparing a phenolic ester with glycolic acid is shown below:

Benzyloxy acetyl chloride ($C_6H_5CH_2OCH_2COCl$) was prepared as described in the following reaction scheme:

Using a similar method, $C_6H_5CH_2OCH(CH_3)COCl$, $C_6H_5CH_2O(CH_2)_5COCl$, and $C_6H_5CH_2OCH_2CH_2OCH_2COCl$ were synthesized for the preparation of phenolic esters.

Lactic acid is a fermentation product of lactose. It is present in sour milk, koumiss, leban, yogurt, and cottage cheese. Lactic acid is produced in the muscles during intense activity. Calcium lactate, a soluble lactic acid salt, serves as a source of calcium in the diet. Lactic acid is produced commercially for use in foods and pharmaceuticals. Many surgical and orthopedic devices, including implantable devices, are made from polylactic acid. The esters of lactic acid are used as emulsifying agents in baking foods (stearoyl-2-lactylate, glyceryl lactostearate, glyceryl lactopalmitate).

Lactic acid can function as both an acid and an alcohol. This dual functionality leads to a variety of chemical reactions and valuable physical properties. The process of preparing a phenolic ester with lactic acid is shown below:

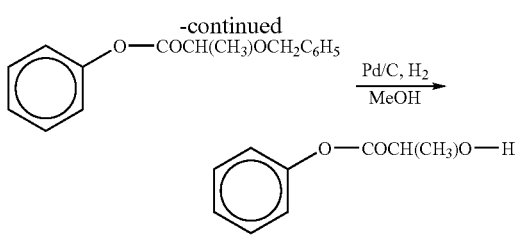

Epsilon-caprolactone is a reactive cyclic monomer, and the polymers derived therefrom are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers.

Epsilon-caprolactone can function as both an acid and an alcohol. This dual functionality leads to a variety of chemical reactions and valuable physical properties. The process of preparing a phenolic ester with epsilon-caprolactone is shown below:

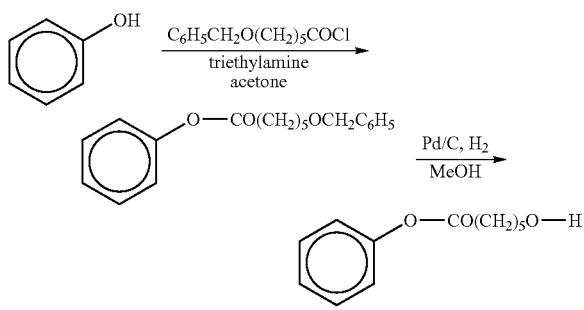

p-Dioxanone (1,4-dioxan-2-one) is a cyclic monomer and polymers are made via ring opening polymerization. Polyesters derived from this monomer are used in making absorbable surgical devices, including implantable devices, with longer absorption profile (slower hydrolysis) compare to polyglycolic acid. The absorbable surgical devices made from 1,4-dioxan-2-one have been proven to be biologically safe, and biocompatible.

p-Dioxanone can function as both an acid and an alcohol. This dual functionality leads to a variety of chemical reactions and valuable physical properties. The process of preparing a phenolic ester with p-dioxanone is shown below:

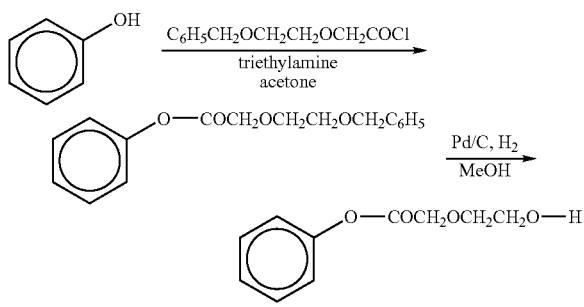

Many species of both the phenolics and the functionalization moieties have been shown to be safe and biocompatible. The new functionalized phenolic compounds have controllable hydrolysis profiles, increased solubility, improved bioavailability, improved efficacy and enhanced functionality. The difunctional compounds can readily polymerize into biodegradable polyesters, polyester amides and polyurethanes, for example, useful for many applications, including biomedical applications, foodstuffs, nutritional supplements, cosmetics, biodegradable chewing gums, flavors, medicaments, coatings and others readily apparent to one skilled in the art.

One aspect of this invention is to combine one or more of these moieties, such as glycolic acid, lactic acid, p-dioxanone, ε-caprolactone, —$CO(CH_2)_mO$—, where m is one of the integers 2, 3, 4 and between 6 and 24 inclusive, and —$COCH_2O(CH_2CH_2O)_n$— where n is an integer between 2 and 24, with phenolic compounds, to form a new chemical entity through an ester forming process. Preferential examples of functionalization molecules are glycolic acid, lactic acid, p-dioxanone, and ε-caprolactone. This functionalization enhances the native value of the phenolic compound while improving its solubility by forming a compound which will controllably release the phenolic moiety into the environment or into the body of a mammalian, preferably a human.

The glycolic ester moiety, lactic ester moiety, dioxanone ester moiety, caprolactone ester moiety, moieties of —$CO(CH_2)_mO$—, where m is one of the integers 2, 3, 4 and between 6 and 24 inclusive, and —$COCH_2O(CH_2CH_2O)_n$— where n is an integer between 2 and 24, have different hydrolysis or degradation rates and times over which they release the active phenolic moiety and thus do the functionalized phenolic compounds made from them. The species used for functionalization supplies the release time or range dictated by the application. Glycolic acid based compounds hydrolyze faster than p-dioxanone based, where as lactic acid and caprolactone based compounds take much longer to hydrolyze than glycolic acid and p-dioxanone based compounds. This desired time range may be obtained by using a combination of functionalized phenolic compounds, that is, a blend of two or more functionalized compounds made from any two or more of the species glycolide, lactide, dioxanone and polydioxanone combined with one phenolic compound.

One aspect of the present invention combines the phenolic compounds with one or more of the ester-forming functionalizing group of compounds to form a functionalized phenolic with uses in medicine, as enhanced drugs, drug intermediates, cancer preventing agents, nutrition supplements, nutriceuticals, antioxidants, controlled release preparations, cosmetic applications, biodegradable chewing gums, flavors, coatings, drug intermediates, solvents for drugs, new monomers for polymerization, and when polymerized, as polymers for biomedical applications, drugs, nutrition supplements, nutriceuticals, drug delivery, cosmetic applications, flavors, and coatings.

The array of functionalized phenolic compounds developed as an aspect of the invention, have a wide range of hydrolysis rates that are controllable. The specific moiety or combination of moieties used for functionalization yield a compound or mixture with specific, controllable hydrolysis ranges.

These new functionalized phenolic compounds have more highly controllable hydrolysis profiles, increased solubility, improved bioavailability, improved efficacy and enhanced functionality. They can be targeted to release the active phenolic component in specific organs or parts of the body. The difunctional compounds polymerize into biodegradable polymers, for example, useful for applications, including biomedical applications, foodstuffs, biodegradable chewing gums, implantable medical devices, cosmetics, medicaments, coatings and other uses readily apparent to one skilled in the art.

The chemical entities disclosed in U.S. Provisional Patent Application Ser. No. US60/647,996 entitled "Functionalized Phenolic Compounds and Polymers There from" are formed through an ether forming process, such as the Williamson Synthesis. These ether-functionalized compounds and their polymers can be used in combination with the ester-functionalized compounds of this invention and their polymers as indicated for further refining the absorption profiles of the mixture.

Synthesis of Phenolic Amides

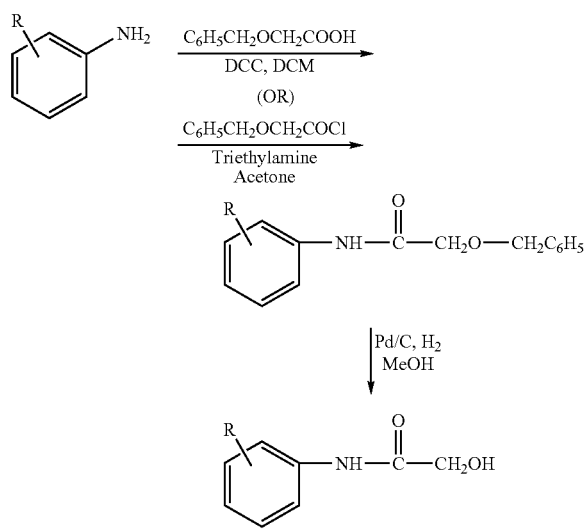

One method of preparing benzyloxyamides is to react benzyloxy acetic acid with an amine using dicyclohexycarbodiimide (DCC) as coupling agent, in dichloromethane (DCM) as a solvent. The amine is dissolved in DCM and benzyloxyacetic acid is added. While maintaining below room temperature, the DCC solution in DCM is added dropwise. The reaction generally proceeds cleanly to form an amide. The urea formed is not soluble in DCM, and the urea can be filtered off to get the amide. In a second method the amines are reacted with the acid chloride directly using a base, such as $K_2CO_3$, $NaHCO_3$ or triethyl amine to neutralize the HCl that is formed during the reaction. Acetone is a good solvent for this reaction. Both methods are suitable for preparing benzyloxyamides.

Synthesis of Phenolic Esters

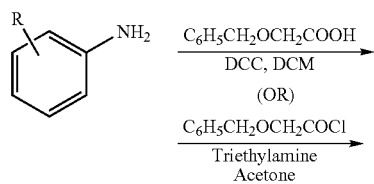

-continued

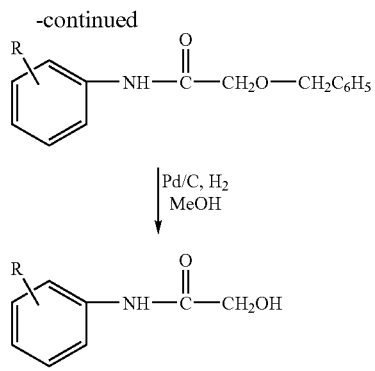

We can use similar conditions as above for preparing benzyloxyesters.

Debenzylation

Debenzylations were done using 50% wet Pd/C (5%) with hydrogen pressure up to 4 kg. MeOH or DMF can be the solvents. Dry Pd/C (5%) can be also used to avoid any moisture, thus avoiding ester hydrolysis. DMF, MeOH, or Ethyl acetate can be used for this reaction.

Examples of the best mode of preparing functionalized phenolic amides and esters are provided for some embodiments of the current invention. It can be extended to many other species. This selection is not meant to limit the scope of the invention in any way. Other variations in the procedure may be readily apparent to those skilled in the art.

Example-1

Benzyloxy-acetic acid 4-(2-benzyloxy-acetoxy)-phenyl ester

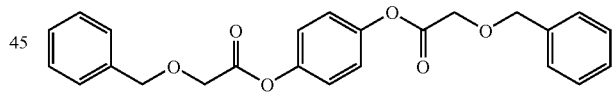

To a mixture of Hydroquinone (10 grams, 90.9 mmol), Triethylamine (51 ml, 366 mmol) in acetone (300 ml) at 10° C. was added Benzyloxy acetyl chloride (50 grams, 271 mmol) drop wise, later stirred at room temperature for 18 hours. Solids were filtered off, acetone distilled and water (100 ml) was added. Crude 1 was extracted into chloroform, washed with 5% sodium bicarbonate solution (2×50 ml), water (2×50 ml), dried over sodium sulphate and distilled. The crude 1 was recrystallised from chloroform:hexane (1:5) to get pure 1 (17 grams, 46%) as a light brown powder. The melting point was measured for all the products by using Polmon (MP 96) melting point apparatus, and the melting point found to be 122-124° C. For all the products, NMR was run using Varian 200 MHz and tetramethylsilane as an internal standard. The structure was confirmed by using NMR.

$^1$H NMR (CDCl$_3$) δ 4.35 (s, 2H, CH$_2$), 4.71 (s, 2H, CH$_2$), 7.14 (s, 2H, CH$_2$), 7.14 (s, 2H, Ar), 7.40 (m, 5H, Ar)

Example-2

Hydroxy-acetic acid 4-(2-hydroxy-acetoxy)-phenyl ester

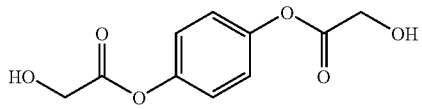

Benzyloxy-acetic acid 4-(2-benzyloxy-acetoxy)-phenyl ester 1 (20 grams, 49.2 mmol) was dissolved in Dimethyl formamide (200 ml) in a pressure vessel, Palladium on carbon (5%, 20 grams) added and the mixture stirred under an atmosphere of hydrogen (4 Kg) for 22 hours. The catalyst was removed by filtration and distilled off the Dimethyl formamide under vacuum. The crude 2 was purified by column chromatography on silica gel using chloroform:Ethyl acetate (95:5) and further purified by recrystallising in chloroform:methanol (5:1) to get pure 2 (3 grams, 27%) as a white powder. The melting point was found to be 162-163° C., and the structure was confirmed by using NMR.

$^1$H NMR (DMSO, d6) δ 4.28 (d, 2H, CH$_2$), 5.58 (t, 1H, OH), 7.20 (s, 2H, Ar)

Example-3

Benzyloxy-acetic acid 4-acetylamino-phenyl ester

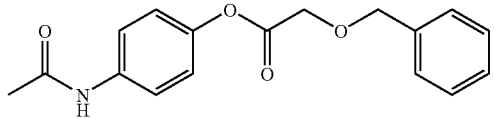

To mixture of Paracetamal (25 grams, 165 mmol) Triethylamine (41.5 grams, 410 mmol) in acetone (250 ml) at 10° C. was added benzyloxy acetyl chloride (40 grams, 217 mmol) drop wise, later stirred at room temperature for 16 hours. The solids were filtered off, acetone distilled and water (200 ml) was added. Crude 3 was extracted into chloroform, washed with 5% sodium bicarbonate solution (2×100 ml), water (2×100 ml), distilled and purified by column chromatography on silica gel using benzene as eluant to get pure 3 (30 grams, 60.7%) as a light brown powder. The melting point was found to be 106-108.8° C., and the structure was confirmed by using NMR.

$^1$H NMR (CDCl$_3$) δ 2.10 (s, 3H, COCH$_3$), 4.30 (s, 2H, CH$_2$), 4.68 (s, 2H, CH$_2$), 6.96 (d, 2H, Ar), 7.31 (m, 5H, Ar), 7.45 (d, 2H, Ar), 7.68 (bs, 1H, NH)

Example-4

Hydroxy-acetic acid 4-acetylamino-phenyl ester

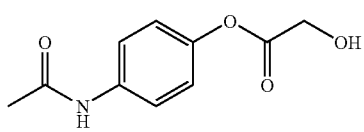

Benzyloxy-acetic acid 4-acetylamino-phenyl ester 3 (15 grams, 50 mmol) was dissolved in methanol (150 ml) in a pressure vessel, palladium on carbon (5%, 8 grams) added and the mixture stirred under an atmosphere of Hydrogen (3 Kg) for 20 hours. The catalyst was removed by filtration and distilled off the methanol. The crude 4 was recrystallised from a mixture of chloroform:methanol (1:4) to get pure 4 (6 grams, 57.2%) as a white powder. The melting point was found to be 144-146° C., and the structure was confirmed by using NMR.

$^1$H NMR (CDCl$_3$+DMSO, d$_6$) δ 2.12 (s, 3H, COCH$_3$), 4.36 (s, 2H, CH$_2$), 5.22 (bs, 1H, OH), 6.98 (d, 2H, Ar), 7.58 (d, 2H, Ar), 9.60 (s, 1H, NH)

Example-5

2-Benzyloxy-N-(4-hydroxy-phenyl)-acetamide

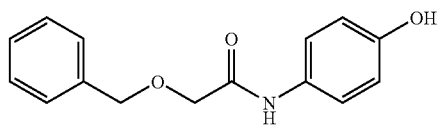

To a mixture of 4-Amino phenol (20 grams, 183.2 mmol) Sodium bicarbonate (17 grams, 202 mmol) in acetone (150 ml) at 0° C. was added Benzyloxy acetyl chloride (40 grams, 216.8 mmol) drop wise, later stirred at room temperature for 20 hours. The solids were filtered off, and poured on to cold water (500 ml). Crude 5 was extracted into chloroform, washed with 5% Sodium bicarbonate solution (2×100 ml), water (2×100 ml), dried over sodium sulphate and distilled. The crude 5 was purified by column chromatography on silica gel using chloroform as eluant to get pure 5 (23 grams, 48.9%) as a light orange syrup. The structure was confirmed by using NMR.

$^1$H NMR (CDCl$_3$) δ 4.00 (s, 2H, CH$_2$), 4.54 (s, 2H, CH$_2$), 6.68 (d, 2H, Ar), 7.22 (m, 7H, Ar), 7.72 (s, 1H, OH), 8.22 (s, 1H, NH)

Example-6

2-Hydroxy-N-(4-hydroxy-phenyl)-acetamide

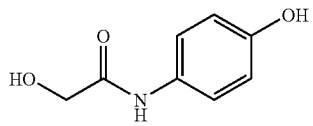

2-Benzyloxy-N-(4-hydroxy-phenyl)-acetamide 5 (18 grams, 70 mmol) was dissolved in methanol (100 ml) in a pressure vessel, Palladium on carbon (5%, 8 grams) added and the mixture stirred under an atmosphere of hydrogen (4 Kg) for 8 hours. The catalyst was removed by filtration and distilled off the methanol. The crude 6 was recrystallised from a mixture of chloroform:methanol (1:5) to get pure 6 (4 grams, 34.2%) as a white shining powder. The melting point was found to be 141-142.6° C., and the structure was confirmed by using NMR.

$^1$H NMR (CDCl$_3$) δ 3.26 (bs, 1H, OH), 4.00 (s, 2H, CH$_2$), 6.68 (d, 2H, Ar), 7.40 (d, 2H, Ar), 8.92 (bs, 1H, NH)

Example-7

Benzyloxy-acetic acid 4-(2-benzyloxy-acetylamino)-phenyl ester

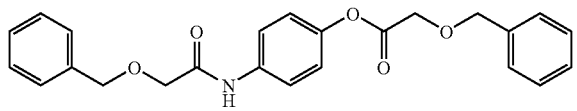

To a mixture of 4-Amino phenol (20 grams, 183.26 mmol), triethylamine (90 grams, 889.41 mmol) in acetone (400 ml) at 0° C. was added benzyloxy acetyl chloride (100 grams, 542 mmol) drop wise, later stirred at room temperature for 18 hours. Solids were filtered off, acetone distilled and water (200 ml) was added. Crude 7 was extracted in to chloroform, washed with 5% sodium bicarbonate (2×100 ml), dried over sodium sulphate and distilled. The crude 7 was purified by column chromatography on silica gel using benzene as eluant to give pure 7 (27 grams, 36.37%) as light brown powder. The melting point was found to be 55.5-58.5° C., and the structure was confirmed by using NMR.

$^1$HNMR (CDCl$_3$) δ 4.02 (s, 2H, OCH$_2$), 4.28 (s, 2H, OCH$_2$), 4.60 (s, 2H, OCH$_2$), 4.70 (s, 2H, OCH$_2$), 7.02 (d, 2H, Ar), 7.32 (m, 10H, Ar), 7.56 (d, 2H, Ar), 8.32 (s, 1H, NH)

Example-8

Hydroxy-acetic acid 4-(2-hydroxy-acetylamino)-phenyl ester

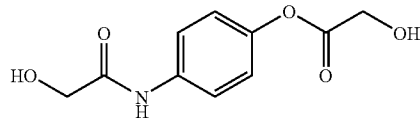

Benzyloxy-acetic acid 4-(2-benzyloxy-acetylamino)-phenyl ester 7 is dissolved in methanol (50 ml) in a pressure vessel, Palladium on carbon (5%, 4 grams) added and the mixture stirred under an atmosphere of hydrogen (4 Kg) for 10 hours. The catalyst is removed by filtration, methanol distilled under vacuum. The crude 8 can be purified by column chromatography on silica gel using benzene:ethyl acetate (8:2) as eluant to get the desired product.

Example-9

(4-Benzyloxy-phenoxy)-acetic acid methyl ester

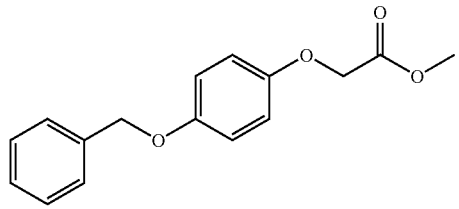

To a mixture of 4-Benzyloxy phenol (40 grams, 200 mmol), anhydrous Potassium carbonate (84 grams, 608 mmol), sodium iodide (4 grams, 27 mmol) in anhydrous acetone (500 ml) was added Methyl chloro acetate (24.3 grams, 224 mmol) and refluxed for 12 hours. Acetone was distilled and water (400 ml) was added. Crude 9 was filtered, dried and recrystallised from a mixture of Ethyl acetate:Hexane (1:5) to give pure 9 (34 grams, 62.5%) as a white fluffy powder. The melting point was found to be 79-80° C., and the structure was confirmed by using NMR.

$^1$H NMR (CDCl$_3$) δ 3.80 (s, 3H, ester), 4.52 (s, 2H, OCH$_2$), 6.00 (s, 2H, OCH$_2$), 6.82 (m, 5H, Ar), 7.35 (m, 4H, Ar)

Example-10

(4-Hydroxy-phenoxy)-acetic acid methyl ester

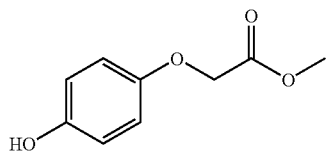

(4-Benzyloxy-phenoxy)-acetic acid methyl ester 9 (40 grams, 147 mmol) was dissolved in dry methanol (1000 ml) in a 3 liter round bottom flask, Palladium on carbon (5%, 13 grams) added, and the mixture stirred under an atmosphere of hydrogen for 10 hours. The catalyst was removed by filtration and the filtrate was distilled to give pure 10 (23 grams, 85.9%) as a white powder. The melting point was found to be 115-117° C., and the structure was confirmed by using NMR.

$^1$H NMR (CDCl$_3$+DMSO d$_6$) δ 3.72 (s, 3H, ester), 4.48 (s, 2H, OCH$_2$), 6.64 (s, 4H, Ar), 8.48 (s, 1H, OH)

Example-11

4-(2-Benzyloxy-acetoxy)-phenoxy]-acetic acid methyl ester

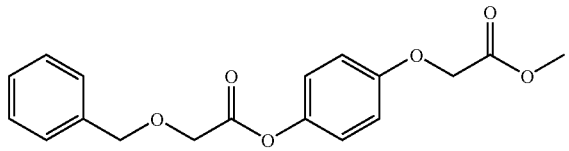

To a mixture of 4-Hydroxy phenoxy)acetic acid methyl ester 10 (5 grams, 26 mmol), Triethylamine (8.2 grams, 81 mmol) in acetone (50 ml) at 0° C. was added benzyloxy acetyl chloride (10 grams, 54.2 mmol) drop wise, later stirred at room temperature for 18 hours. Solids were filtered off and poured onto cold water (100 ml). Crude 11 was extracted into chloroform, washed with 5% sodium bicarbonate solution (2×50 ml), water (2×50 ml), dried over sodium sulphate and distilled. The crude 11 was purified by column chromatography on silica gel using benzene as eluant to get pure 11 (5 grams, 58.2%) as light brown powder. The melting point was found to be 54-56° C., and the structure was confirmed by using NMR.

$^1$H NMR (CDCl$_3$) δ 3.75 (s, 3H, Ester), 4.24 (s, 2H, CH$_2$), 4.55 (s, 2H, CH$_2$), 4.66 (s, 2H, CH$_2$), 6.80 (d, 2H, Ar), 6.96 (d, 2H, Ar), 7.30 (m, 5H, Ar)

Example-12

[4-(2-Hydroxy-acetoxy)-phenoxy]-acetic acid methyl ester

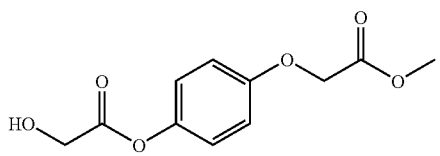

4-(2-Benzyloxy-acetoxy)-phenoxy]-acetic acid methyl ester 11 (5 grams) was dissolved in methanol (50 ml) in a pressure vessel, palladium on carbon (5%, 5 grams) added and the mixture stirred under an atmosphere of hydrogen (4 Kg) for 4 hours. The catalyst was removed by filtration and distilled off the methanol. The crude 12 was recrystallised from a mixture of chloroform:Hexane (1:6) to get pure 12 (1.6 grams, 44%) as a white powder. The melting point was found to be 92-94.5° C., and the structure was confirmed by using NMR.

$^1$H NMR (CDCl$_3$+DMSO, d$_6$) δ 3.78 (s, 3H, Ester), 4.28 (s, 2H, CH$_2$OH), 4.62 (s, 2H, OCH$_2$), 5.14 (t, 1H, OH), 6.86 (d, 2H, Ar), 7.00 (d, 2H, Ar)

Example-13

2-(4-Benzyloxy-phenoxy)-propionic acid methyl ester

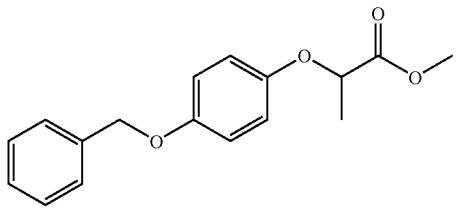

To a mixture of 4-Benzyloxy phenol (50 grams, 250 mmol), anhydrous Potassium carbonate (138 grams, 1000 mmol), sodium iodide (20 grams, 130 mmol), disodium phosphate (20 grams, 140 mmol) in anhydrous acetone (750 ml) was added methyl 2-Chloro Propionate (40 grams, 330 mmol) and refluxed for 48 hrs. Acetone was distilled and water (800 ml) was added. Crude 13 was filtered, dried and recrystallised from a mixture of chloroform:hexane (1:6) to give pure 13 (60 grams, 84%) as a white power. The melting point was found to be 67.5-68.5° C., and the structure was confirmed by using NMR.

$^1$H NMR (CDCl$_3$) δ 1.58 (d, 3H, CH$_3$), 3.74 (s, 3H, ester), 4.64 (q, 1H, OCH), 5.00 (s, 2H, OCH$_2$), 6.78 (m, 4H, Ar), 7.30 (m, 5H, Ar)

Example-14

2-(4-Hydroxy-phenoxy)-propionic acid methyl ester

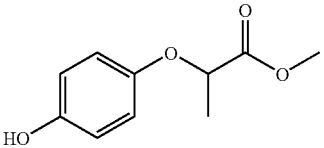

2-(4-Benzyloxy-phenoxy)-propionic acid methyl ester 13 (50 grams, 170 mmol) was dissolved in dry Dimethyl formamide (500 ml) in pressure vessel, Palladium on carbon (5%, 25 grams) added, and the mixture stirred under an atmosphere of Hydrogen (2.5 Kg) for 7 hrs. The catalyst was removed by filtration and the filtrate was diluted with water (2000 ml). Crude 14 was extracted into ether, dried over sodium sulphate, distilled and purified by column chromatography on silica gel using chloroform as eluant to give pure 14 (30 grams, 88%) as a syrup. The structure was confirmed by using NMR.

$^1$H NMR (CDCl$_3$) δ 1.62 (d, 3H, CH$_3$), 3.76 (s, 3H, Ester), 4.68 (q, 1H, OCH), 4.84 (bs, 1H, OH), 6.76 (s, 4H, Ar)

Example-15

2-[4-(2-Benzyloxy-acetoxy)-phenoxy]-propionic acid methyl ester

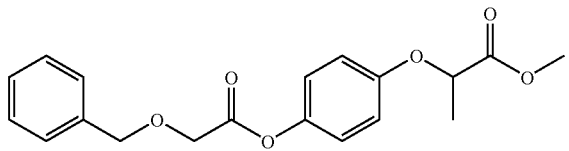

To a mixture of 2(4-Hydroxyphenoxy)propionic acid methyl ester 14 (2 grams, 10.2 mmol), Trietylamine (3.2 grams, 31.6 mmol) in acetone (30 ml) at 0° C. was added benzyloxy acetyl chloride (4.9 grams, 26.5 mmol) drop wise, later stirred at room temperature for 40 hours. The solids were filtered off, acetone distilled and cold water (20 ml) was added. Crude 15 was extracted into chloroform, washed with 5% sodium bicarbonate solution (2×10 ml), water (2×10 ml), dried over sodium sulphate and distilled. The crude 15 was purified by column chromatography on silica gel using benzene as eluant to give pure 15 (2.4 grams, 68.45%) as a light yellow syrup. The structure was confirmed by using NMR.

$^1$H NMR (CDCl$_3$) δ 1.62 (d, 3H, CH$_3$), 3.75 (s, 3H, Ester), 4.38 (s, 2H, CH$_2$), 4.68 (s&t, 3H, CH&CH$_2$), 6.82 (d, 2H, Ar), 6.98 (d, 2H, Ar), 7.34 (m, 5H, Ar)

Example-16

2-[4-(2-Hydroxy-acetoxy)-phenoxy]-propionic acid methyl ester

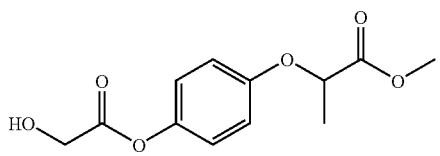

2-[4-(2-Benzyloxy-acetoxy)-phenoxy]-propionic acid methyl ester 15 (13 grams, 37.79 mmol) is dissolved in methanol (100 ml) in a pressure vessel, palladium on carbon (50% wet, 5%, 10 grams) added and the mixture stirred under an atmosphere of hydrogen (4 Kg) for 48 hours. The catalyst is removed by filtration and distilled off the methanol. The crude 16 can be purified by column chromatography on silica gel using chloroform:Ethyl acetate.

Example-17

6-(4-Benzyloxy-phenoxy)-hexanoic acid methyl ester

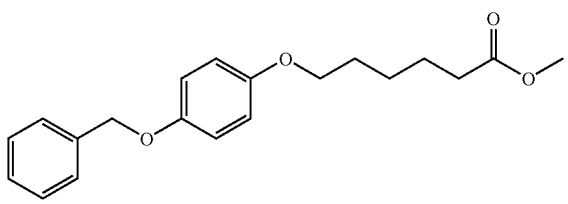

To a mixture of 4-Benzyloxy phenol (100 grams, 490 mmol), anhydrous potassium carbonate (276 grams, 1.99 moles), sodium iodide (25 grams, 160 mmol), Disodium phosphate (25 grams, 170 mmol) in anhydrous acetone (1500 ml) was added Methyl 6-bromo hexanoate (135 grams, 640 mmol) and refluxed for 68 hrs. Acetone was distilled and water (1500 ml) was added. Crude 17 was filtered, dried and recrystallised from a mixture of chloroform:hexane (1:6) to give pure 17 (120 grams, 73%) as a white power. The melting point was found to be 85-87° C., and the structure was confirmed by using NMR.

$^1$H NMR (CDCl$_3$) δ 1.52 (m, 2H, CH$_2$), 1.75 (m, 4H, CH$_2$), 2.38 (t, 2H, CH$_2$), 3.68 (s, 3H, ester), 3.94 (t, 2H, OCH$_2$), 5.04 (s, 2H, OCH$_2$), 6.82 (m, 4H, Ar), 7.38 (m, 5H, Ar)

Example-18

6-(4-Hydroxy-phenoxy)-hexanoic acid methyl ester

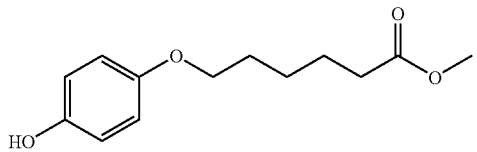

6-(4-Benzyloxy-phenoxy)-hexanoic acid methyl ester 17 (35 grams, 110 mmol) was dissolved in dry Dimethyl formamide (350 ml) in a pressure vessel, Palladium on carbon (5%, 17.5 grams) added, and the mixture stirred under an atmosphere of hydrogen (3 Kg) for 6 hours. The catalyst was removed by filtration and the filtrate was diluted with water (1500 ml). Crude 18, was filtered, washed with water, dried to give pure 18 (22 grams, 87%) as a white power. The melting point was found to be 56-58.5° C., and the structure was confirmed by using NMR.

$^1$H NMR (CDCl$_3$) δ 1.54 (m, 2H, CH$_2$), 1.78 (m, 4H, CH$_2$), 2.35 (t, 2H, CH$_2$), 3.68 (s, 3H, ester), 3.85 (t, 2H, OCH$_2$), 4.90 (s, 1H, OH), 6.70 (s, 4H, Ar)

Example-19

6-[4-(2-Benzyloxy-acetoxy)-phenoxy]-hexanoic acid methyl ester

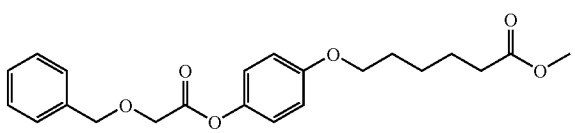

To a mixture of 6-(4-Hydroxyphenoxy)hexanoic acid methyl ester 18 (15 grams, 63 mmol), Triethylamine (29 grams, 286.6 mmol) in acetone (200 ml) at 0° C. was added benzyloxy acetyl chloride (35 grams, 189.7 mmol) drop wise, later stirred at room temperature for 20 hours. The solids were filtered off, acetone distilled and cold water (200 ml) was added. Crude 19 was extracted into chloroform, washed with 5% sodium bicarbonate (2×100 ml), water (2×100 ml), dried over sodium sulphate and distilled. The crude 19 was purified by column chromatography on silica gel using benzene as eluant to give pure 19 (18.5 grams, 76%) as a light brown syrup. The structure was confirmed by using NMR.

$^1$H NMR (CDCl$_3$) δ 1.50 (m, 2H, CH$_2$), 1.78 (m, 4H, CH$_2$X2), 2.32 (t, 2H, CH$_2$), 3.64 (s, 3H, Ester), 3.90 (t, 2H, OCH$_2$), 4.26 (s, 2H, CH$_2$), 4.68 (s, 2H, CH$_2$), 6.78 (d, 2H, Ar), 6.95 (d, 2H, Ar), 7.30 (m, 5H, Ar)

Example-20

6-[4-(2-Hydroxy-acetoxy)-phenoxy]-hexanoic acid methyl ester

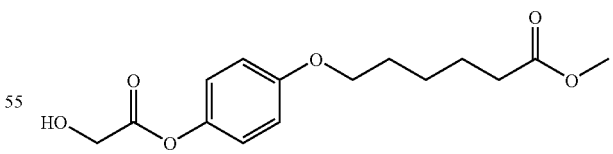

6-[4-(2-Benzyloxy-acetoxy)-phenoxy]-hexanoic acid methyl ester 19 (15 grams, 38.86 mmol) is dissolved in methanol (100 ml) in a pressure vessel, palladium on carbon (50% wet, 5%, 15 grams) added and the mixture stirred under an atmosphere of hydrogen (4 Kg) for 48 hours. The catalyst is removed by filteration and distilled off the methanol. The crude can be purified by column chromatography on silica gel using chloroform as eluant.

Example 21

(4-Acetylamino-phenoxy)-acetic acid ethyl ester

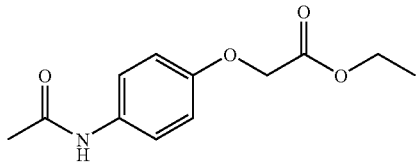

To a mixture of Paracetamol (300 grams, 1.984 mol), anhydrous $K_2CO_3$ (1.80 Kg, 7.814 mmol) in anhydrous Acetone (3 liters) was added ethyl bromo acetate (452 grams, 2.7 mol) and refluxed for 16 Hours. Acetone was distilled and water (5 liter) was added. Crude 21 was filtered, dried and recrystallised from a mixture of toluene:Hexane (1:5) to give pure 21 (377 grams, 80%) as a white shining powder. The melting point was found to be 104.2-106.2° C.

Example 22

(4-Amino-phenoxy) acetic acid HCl

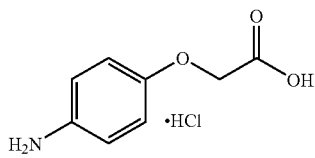

A mixture (4-Acetylamino-phenoxy)-acetic acid ethyl ester 21 (375 grams, 1.582 mmol), in concentrated Hydrochloric acid (9.36 liters) was refluxed for 12 Hours. Excess concentrated Hydrochloric acid was distilled off in vacuum and filtered hot. The mixture was cooled to 10° C., filtered and dried to give pure 22 (250 grams, 77.6%) as a wheat colored powder. The melting point was found to be 224-226° C., and the structure was confirmed by using NMR.

$^1$H NMR ($D_2O$) δ 4.68 (s, 2H, $OCH2$), 3.65 (s, 3H, ester), 7.0 (d, 2H, Ar), 7.30 (d, 2H, Ar

Example 23

(4-Amino-phenoxy)-acetic acid methyl ester

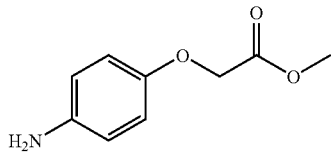

To a mixture (4-Amino-phenoxy) acetic acid HCl 22 (250 grams, 1.228 mol), in methanol (5 liters) was passed dry HCl gas at 10° C. for 1 hour and refluxed for 10 hours. Methanol (3.5 liters) was distilled and ice water (1 liter) was added and the pH was adjusted to 7.5 with $K_2CO_3$. Crude 23 was filtered, dried and recrystallised from a mixture of Chloroform:Hexane (1:5) to give pure 23 (130 grams, 58.5%) as a light brown powder. The melting point was found to be 65-66.8° C.

Example-24

[4-(2-Benzyloxy-acetylamino)-phenoxy]-acetic acid methyl ester

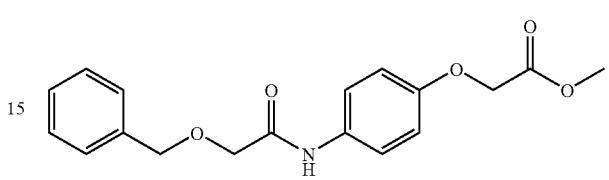

To a mixture of (4-Amino phenoxy)-acetic acid methyl ester 23 (20 grams, 110.5 mmol) benzyloxy acetic acid (20.4 grams, 123 mmol) in anhydrous Dichloromethane (200 ml) under nitrogen atmosphere was added a solution of 1,3-Dicyclohexyl carbodiimide (63.2 grams, 306 mmol) in anhydrous Dichloromethane (80 ml) drop wise. The reaction mixture was stirred at room temperature for 12 hours. The solids were filtered off, the Dichloromethane was washed with 5% sodium bicarbonate solution (100 ml), water (100 ml), dried over sodium sulphate, distilled to get crude 24. The crude 24 was purified by column chromatography on silica gel using benzene as eluant to get pure 24 (25 grams, 68.9%) as a white powder. The melting point was found to be 76-77.5° C., and the structure was confirmed by using NMR.

$^1$H NMR ($CDCl_3$) δ 3.82 (s, 3H, ester), 4.10 (s, 2H, $CH_2$), 4.62 (s, 2H, $CH_2$), 4.66 (s, 2H, $CH_2$), 6.88 (d, 2H, Ar), 7.38 (m, 5H, Ar), 7.46 (d, 2H, Ar), 8.24 (bs, 1H, NH)

Example-25

[4-(2-Hydroxy-acetylamino)-phenoxy]-acetic acid methyl ester

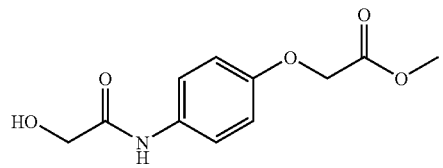

[4-(2-Benzyloxy-acetylamino)-phenoxy]-acetic acid methyl ester 24 (25 grams, 76 mmol) was dissolved in methanol (450 ml) in a pressure vessel, palladium on carbon (5%, 10 grams) added and the mixture stirred under an atmosphere of hydrogen (2 Kg) for 5 hours. The catalyst was removed by filtration and distilled off the methanol. The crude 25 was recrystallised in chloroform:Hexane (1:6) to give pure 25 (14 grams) as a white powder. The melting point was found to be 147.5-150° C., and the structure was confirmed by using NMR.

$^1$H NMR ($CDCl_3$+DMSO-$d_6$): δ 3.74 (s, 3H, ester), 3.96 (d, 2H, $CH_2OH$), 4.64 (s, 2H, $OCH_2$), 5.48 (t, 1H, OH), 6.80 (d, 2H, Ar), 7.54 (d, 2H, Ar) 9.2 (bs, 1H, NH)

Example 26

2-(4-Acetylamino-phenoxy)-propionic acid methyl ester

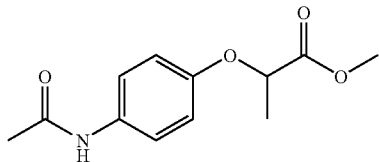

To a mixture of Paracetamol (150 grams, 992 mmol), anhydrous $K_2CO_3$ (540 Kg, 3.91 mol), sodium iodide (18 grams, 120 mmol) in anhydrous Acetone (3 liters) was added methyl 2-chloro propionate (180 grams, 1.469 mmol) and refluxed for 80 Hours. Acetone was distilled and water (3 liter) was added. Crude 26 was extracted into chloroform, dried over $Na_2SO_4$, distilled and added hexane (750 ml), filtered and recrystallised in methanol to give pure 26 (95 grams, 40.4%) as a white powder. The melting point was found to be 96.5-98.2° C., and the structure was confirmed by using NMR.

$^1$H NMR (CDCl$_3$) δ 1.60 (d, 3H, CH$_3$), 2.08 (s, 3H, O=C—CH$_3$), 3.76 (s, 3H, ester), 4.66 (q, 1H, CH), 6.72 (d, 2H, Ar), 7.32 (d, 2H, Ar), 8.04 (bs, 1H, NH)

Example 27

2-(4-Amino-phenoxy)-propionic acid

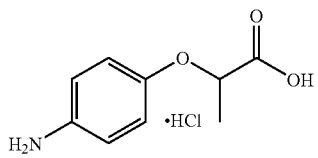

To a mixture 2-(4-Acetylamino-phenoxy)-propionic acid methyl ester 26 (320 grams, 1.35 mol) in concentrated Hydrochloric acid (8 liters) was refluxed for 48 hours. Excess concentrated Hydrochloric acid was distilled in vacuum and filtered hot. The mixture was cooled to 10° C., filtered and dried to give pure 27 (240 grams, 81.7%) as a brown powder. The melting point was found to be 175-180° C.

Example 28

2-(4-Amino-phenoxy)-propionic acid methyl ester

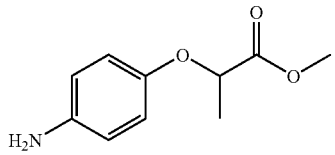

To a mixture of 2-(4-Amino-phenoxy)-propionic acid 27 (240 grams, 1.103 mmol), in Methanol (4.8 liters) was passed dry HCl gas at 10° C. for 1 hour and refluxed for 48 hours. Methanol (2.5 liter) was distilled, ice water (1 liter) was added and the pH was adjusted to 7.5 with $K_2CO_3$. Crude 28 was extracted into chloroform, washed with 5% NaHCO$_3$ solution, water, dried over $Na_2SO_4$ and distilled to give 28 (80 grams, 37.2%) as a brown syrup. The structure was confirmed by using NMR.

$^1$H NMR (CDCl$_3$) δ 1.56 (d, 3H, CH$_3$), 2.9 (bs, 2H, —NH$_2$), 3.72 (s, 3H, ester), 4.58 (q, 1H, CH), 6.53 (d, 2H, Ar), 6.68 (d, 2H, Ar)

Example-29

2-[4-(2-Benzyloxy-acetylamino)-phenoxy]-propionic acid methyl ester

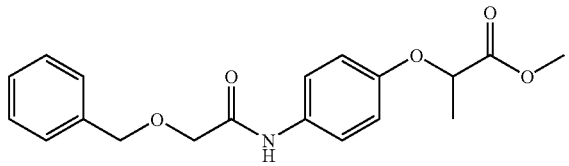

To a mixture of 2-(4-Amino phenoxy)-propionic acid methyl ester 28 (20 grams, 102.5 mmol), Triethylamine (23 ml, 165 mmol) in acetone (120 ml) at 0° C. was added benzyloxy acetyl chloride (28 grams, 152 mmol) drop wise, later stirred at room temperature for 12 hours. The solids were filtered off, acetone distilled and water (100 ml) was added. Crude 29 was extracted into chloroform, washed with 5% sodium bicarbonate (2×100 ml), water (200 ml), dried over sodium sulphate and distilled. The crude 29 was purified by column chromatography on silica gel using benzene as eluant to get pure 29 (21 grams, 59.8%) as a light brown powder. The melting point was found to be 67-70° C., and the structure was confirmed by using NMR.

$^1$H NMR (CDCl$_3$) δ 1.60 (d, 3H, CH$_3$), 3.72 (s, 3H, Ester), 4.02 (s, 2H, CH$_2$), 4.62 (s, 2H, CH$_2$), 4.68 (q, 1H, CH), 6.76 (d, 2H, Ar), 7.30 (m, 5H, Ar), 7.42 (d, 2H, Ar), 8.18 (s, 1H, NH)

Example-30

2-[4-(2-Hydroxy-acetylamino)-phenoxy]-propionic acid methyl ester

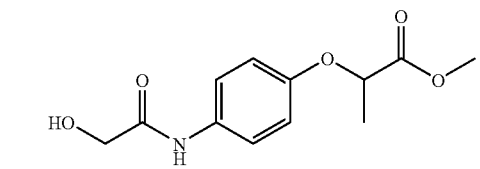

2-[4-(2-Benzyloxy-acetylamino)-phenoxy]-propionic acid methyl ester 29 (15 grams, 43.7 mmol) was dissolved in methanol (150 ml) in a pressure vessel, palladium on carbon (5%, 8 grams) added and the mixture stirred under an atmosphere of hydrogen (2.5 Kg) for 10 hours. The catalyst was removed by filtration and distilled off the methanol. The crude 30 was recrystallised in chloroform:hexane (1:6) to give pure 30 (4 grams, 36.3%) as a white powder. The melting point was found to be 111-112.6° C., and the structure was confirmed by using NMR.

$^1$H NMR (CDCl$_3$) δ 1.60 (d, 3H, CH$_3$), 3.44 (bt, 1H, OH), 3.78 (s, 3H, Ester), 4.14 (d, 1H, CH$_2$OH), 4.72 (q, 1H, CH), 6.80 (d, 2H, Ar), 7.44 (d, 2H, Ar), 8.30 (s, 1H, NH)

Example 31

6-(4-Acetylamino-phenoxy)-hexanoic acid methyl ester

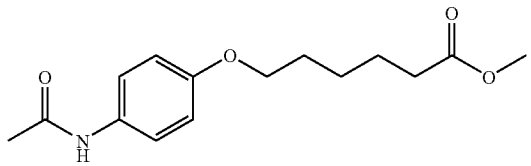

To a mixture of Paracetamol (250 grams, 1.654 mmol), anhydrous $K_2CO_3$ (800 grams, 5.789 mmol), sodium iodide (17 grams, 113 mmol) in anhydrous Acetone (5 liters) was added methyl 6-bromo hexanoate (470 grams, 2.25 mmol) and refluxed for 60 Hours. Acetone was distilled and water (3 liter) was added. Crude 31 was filtered, dried and recrystallised from a mixture of chloroform:Hexane (1:5) to give pure 31 (195 grams, 66%) as a white powder. The melting point was found to be 96.4-98.8° C., and the structure was confirmed by using NMR.

$^1$H NMR (CDCl$_3$) δ 1.54 (m, 2H, CH$_2$), 1.80 (m, 4H, CH$_2$), 2.14 (s, 3H, O=C—CH$_2$), 2.38 (t, 2H, CH$_2$), 3.68 (s, 3H, ester), 3.92 (t, 2H, OCH$_2$), 6.68 (d, 2H, Ar), 7.05 (bs, 1H, NH), 7.38 (d, 2H, Ar).

Example 32

6-(4-Amino-phenoxy)-hexanoic acid hydrochloride

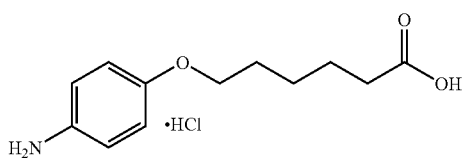

To a mixture of 6-(4-Acetylamino-phenoxy)-hexanoic acid methyl ester 31 (290 grams, 1.04 moles), in concentrated Hydrochloric acid (7.12 Liter) was refluxed for 48 hours. Excess concentrated Hydrochloric acid was distilled off in vacuum and filtered hot. The mixture was cooled to 10° C., filtered and dried give pure 32 (150 grams, 55.6%) as a brown powder. The melting point was found to be 155-160° C.

Example 33

6-(4-Amino-phenoxy)-hexanoic acid methyl ester

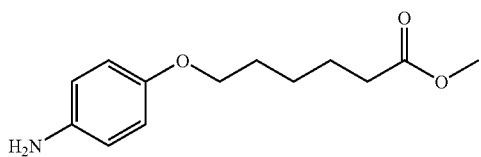

To a mixture of 6-(4-Amino-phenoxy)-hexanoic acid Hydrochloride 32 (150 grams, 578 mmol), in methanol (3 liters) was passed dry HCl gas at 10° C. for 1 hour and refluxed for 48 hours. Methanol (1.5 liter) was distilled, ice water (1 liter) was added and the pH was adjusted to 7.5 with $K_2CO_3$. Crude 33 was extracted into chloroform, washed with 5% NaHCO$_3$ solution, water, dried over Na$_2$SO$_4$ and distilled to give 33 (60 grams, 43.8) as a thick brown syrup. The structure was confirmed by using NMR.

$^1$H NMR (CDCl$_3$) δ 1.5 (m, 2H, CH$_2$), 1.72 (m, 4H, CH$_2$), 2.34 (t, 2H, CH$_2$), 3.66 (s, 3H, ester), 3.85 (t, 2H, OCH$_2$), 6.56 (d, 2H, Ar), 6.68 (d, 2H, Ar).

Example-34

6-[4-(2-Benzyloxy-acetylamino)-phenoxy]-hexanoic acid methyl ester

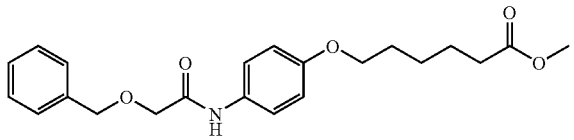

To a mixture of 6-(4-Aminophenoxy)-hexanoic acid methyl ester 33 (25 grams, 105 mmol), triethylamine (21.4 grams, 211.6 mmol) in acetone (200 ml) at 0° C. was added benzyloxy acetyl chloride (25 grams, 135.5 mmol) drop wise, later stirred at room temperature for 12 hours. The solids were filtered off, acetone distilled and water (100 ml) was added. Crude 34 was extracted into chloroform, washed with 5% sodium bicarbonate solution (2×100 ml), water (100 ml), dried over sodium sulphate and distilled. The crude 34 was purified by column chromatography on silica gel using benzene as eluant to get pure 34 (9 grams, 22.2%) as a off-white powder. The melting point was found to be 46-49° C., and the structure was confirmed by using NMR.

$^1$H NMR (CDCl$_3$) δ 1.52 (m, 2H, CH$_2$), 1.72 (m, 4H, CH$_2$X2), 2.32 (t, 2H, CH$_2$), 3.68 (s, 3H, Ester), 3.92 (t, 2H, CH$_2$), 4.10 (s, 2H, CH$_2$), 4.68 (s, 2H, CH$_2$), 6.82 (d, 2H, Ar), 8.20 (s, 1H, NH)

Example-35

6-[4-(2-Hydroxy-acetylamino)-phenoxy]-hexanoic acid methyl ester

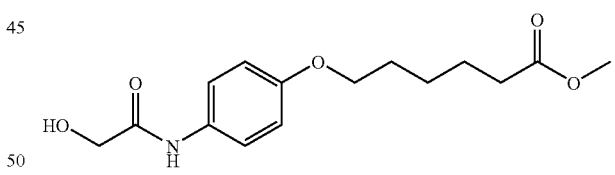

6-[4-(2-Benzyloxy-acetylamino)-phenoxy]-hexanoic acid methyl ester 34 (1 grams, 2.6 mmol) was dissolved in methanol (10 ml) in a pressure vessel, palladium on carbon (5%, 250 mg) added and the mixture stirred under an atmosphere of hydrogen (2 Kg) for 5 hours. The catalyst was removed by filtration and distilled off the methanol. The crude 35 was recrystallised in chloroform:Hexane (1:6) to get pure 35 (0.5 grams, 65.3%) as a white powder. The melting point was found to be 91.5-94° C., and the structure was confirmed by using NMR.

$^1$H NMR (CDCl$_3$) δ 1.45 (m, 2H, CH$_2$), 1.62 (m, 4H, CH$_2$x2), 2.36 (t, 2H, CH$_2$), 3.02 (t, 2H, CH$_2$), 3.02 (t, 1H, OH), 3.68 (s, 3H, Ester), 3.92 (t, 2H, CH$_2$), 4.22 (d, 2H, CH$_2$), 6.84 (d, 2H, Ar), 7.46 (d, 2H, Ar), 8.24 (bs, 1H, NH)

Example 36

2-(6-Hydroxy-naphthalen-2-yl)-propionic acid

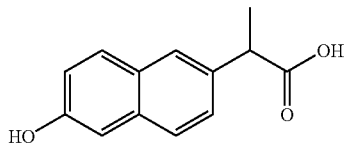

A mixture of Naproxen (500 grams, 2.774 mmol) and 48% HBr (1500 ml) was refluxed for 10 Hours, poured onto ice water (3000 ml) and stirred for 30 minutes. Crude 36 was filtered, dried (380 grams, 81%) and used as such for next stage.

Example 37

2-(6-Hydroxy-naphthalen-2-yl)-propionic acid methyl ester

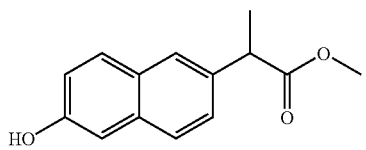

To a solution of methanol (2100 ml) and sulphuric acid (84 ml) was added 2-(6-Hydroxy-naphthalen-2-yl)-propionic acid 36 (420 grams, 1.944 mmol), and refluxed for 6 Hours. Methanol (1000 ml) was distilled and the cooled reaction mass was poured onto ice water (3000 ml) Crude 37 was filtered, dried and recrystallised from a mixture of Ethyl acetate:Hexane (1:5) to give pure 37 (400 grams, 89.5%) as a white fluffy powder. The melting point was found to be 89.5-92° C.

Example-38

2-[6-(2-Benzyloxy-acetoxy)-naphthalen-2-yl]-propionic acid methyl ester

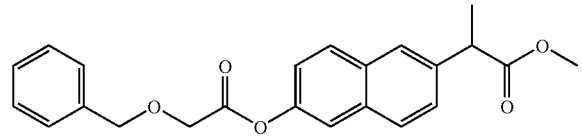

To a mixture of 2-(6-Hydroxy-naphthalen-2-yl)-propionic acid methyl ester 37 (20 gms, 86.95 mmol) Triethyl amine (22.5 gms, 222.35 mmol) in acetone (300 ml) was added benzyloxy acetyl chloride (24 gms, 130 mmol) drop wise and further stirred for 2 hrs at room temperature. The solids were filtered off, acetone distilled and water (100 ml) was added. Crude 38 was extracted into chloroform, washed with 5% sodium bicarbonate (2×50 ml), water (2×50 ml), dried over sodium sulphate and distilled. The crude 38 was purified by recrystallising in chloroform:Hexane (1:6) to get pure 38 (21 gms, 63.9%) as a white powder. The melting point was found to be 58-60° C., and the structure was confirmed by using NMR.

$^{1}$HNMR (CDCl$_3$) δ 1.60 (d, 3H, CH$_3$), 3.68 (s, 3H, Ester), 3.86 (q, 1H, CH), 4.38 (s, 2H, CH$_2$), 4.76 (s, 1H, CH$_2$), 7.20 (d, 1H, Ar), 7.36 (m, 5H, Ar), 7.54 (s, 1H, Ar), 7.78 (m, 4H, Ar)

Example-39

2-[6-(2-Hydroxy-acetoxy)-naphthalen-2-yl]-propionic acid methyl ester

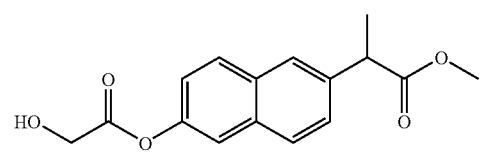

2-[6-(2-Benzyloxy-acetoxy)-naphthalen-2-yl]-propionic acid methyl ester 38 (5 gms, 13.22 mmol) was dissolved in Ethyl acetate (50 ml) in a pressure vessel, palladium on carbon (5%, 3 gms) added and the mixture stirred under an atmosphere of Hydrogen (3.5 Kg) for 4 hrs. The catalyst was removed by filtration and distilled off Ethyl acetate under vacuum. Hexane was added to precipitate, filtered to give pure 39 (3 gms, 78.9%) as off-white powder. The melting point was found to be 49.5-52° C., and the structure was confirmed by using NMR.

$^{1}$HNMR (CDCl$_3$) δ 1.60 (d, 3H, CH$_3$), 3.70 (s, 3H, Ester), 3.90 (q, 1H, CH), 4.50 (s, 2H, CH$_2$), 7.22 (dd, 1H, Ar), 7.48 (dd, 1H, Ar), 7.58 (d, 1H, Ar), 7.80 (m, 3H, Ar)

Example-40

4-(2-Benzyloxy-acetoxy)-benzoic acid methyl ester

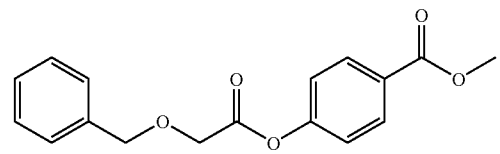

To a mixture of methyl 4-hydroxy benzoate (2 grams, 13.14 mmol), Benzyloxy acetic acid (3.8 grams, 22.86 mmol) in anhydrous Dichloromethane (30 ml) under Nitrogen atmosphere at 0° C. was added a solution of 1,3-Dicyclohexyl carbodiimide (9.5 grams, 46.04 mmol) in anhydrous Dichloromethane (10 ml) drop wise. The reaction mixture was stirred at room temperature for 24 hours. The solids were filtered off, the Dichloromethane was washed with 5% sodium bicarbonate solution (2×10 ml), water (2×10 ml), dried over sodium sulphate, distilled to get crude 40. The crude 40 was purified by column chromatography on silica gel using chloroform as eluant to get pure 40 (1.5 grams, 38%) as a white powder. The melting point was found to be 69.7-71° C., and the structure was confirmed by using NMR.

$^{1}$HNMR (COCl$_3$) δ 3.80 (s, 3H, ester), 4.32 (s, 2H, CH$_2$), 4.70 (s, 2H, CH$_2$), 7.18 (d, 2H, Ar), 7.32 (m, 5H, Ar), 8.18 (d, 2H, Ar)

Example-41

4-(2-Hydroxy-acetoxy)-benzoic acid methyl ester

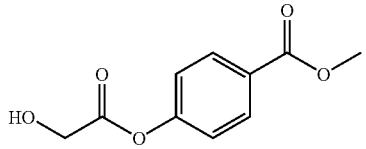

4-(2-Benzyloxy-acetoxy)-benzoic acid methyl ester 40 (2 grams, 6.66 mmol) is dissolved in methanol (50 ml) in a pressure vessel, palladium on carbon (50% wet, 5%, 5 grams) added and the mixture stirred under an atmosphere of hydrogen (4 Kg) for 16 hours. The catalyst is removed by filtration and distilled off the methanol. The crude 41 can be crystallized from a mixture of chloroform:hexane (1:6) to get the desired product.

Example-42

Benzyloxy-acetic acid 4-[7-(2-benzyloxy-acetoxy)-4-oxo-4H-chromen-3-yl]-phenyl ester

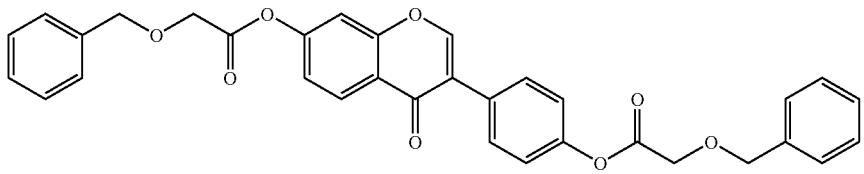

To a mixture of Daidzein (5 grams, 19.66 mmol), triethyl amine (7.26 grams, 71.74 mmol) in dimethyl formamide (50 ml) at 80° C. was added benzyloxy acetyl chloride (10.8 grams, 58.5 mmol) drop wise, later stirred at 80° C. for 3 hours. The reaction mixture was cooled at room temperature, the solids were filtered off and cold water (200 ml) was added, the crude 42 was filtered, dried and recrystallised in ethyl acetate to give pure 42 (3 grams, 27.7%) as white powder. The melting point was found to be 147-148.5° C., and the structure was confirmed by using NMR.

$^1$HNMR (CDCl$_3$) δ 4.34 (s, 2H, CH$_2$), 4.36 (s, 2H, CH$_2$), 4.72 (s, 4H, CH$_2$x2), 7.18 (m, 4H, Ar), 7.36 (m, 10H, Ar), 7.56 (d, 2H, Ar), 8.00 (s, 1H, Ar), 8.30 (s, 1H, Ar)

Example-43

Hydroxy-acetic acid 4-[7-(2-hydroxy-acetoxy)-4-oxo-4H-chromen-3-yl]-phenyl ester

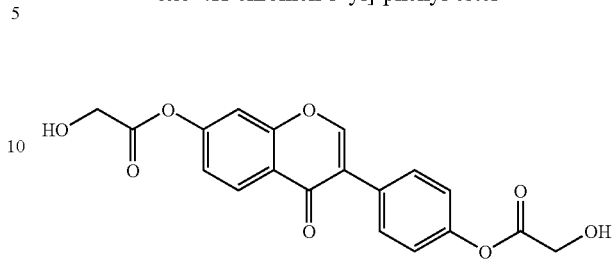

Benzyloxy-acetic acid 4-[7-(2-benzyloxy-acetoxy)-4-oxo-4H-chromen-3-yl]-phenyl ester 42 (1 gram, 1.82 mmol) is dissolved in ethyl acetate (50 ml) in a pressure vessel, Palladium on carbon (5%, 0.5 gram) added and the mixture stirred under an atmosphere of hydrogen (4 Kg) for 22 hours. The catalyst is removed by filtration, ethyl acetate distilled under vacuum. The crude 43 can be purified by column chromatography on silica gel using benzene:ethyl acetate (8:2) as eluant to get the desired product.

In Vitro Hydrolysis of Functionalized Phenolics

A few selected compounds were examined for the rate of hydrolysis by conducting in vitro hydrolysis studies at reflux temperature (100° C.). For each experiment, 500 mg of a functionalized compound and 50 ml of pH 7.4 buffer solution (purchased from Aldrich chemical company) were charged into a 100 ml round bottom flask fitted with a condenser and the contents were refluxed. In vitro hydrolysis of the functionalized phenolics was monitored by thin layer chromatography (TLC) using corresponding starting material (original phenolic) as a control. In vitro hydrolysis was continued at reflux until the functionalized molecule hydrolyzed to the starting phenolic compound.

Example-44

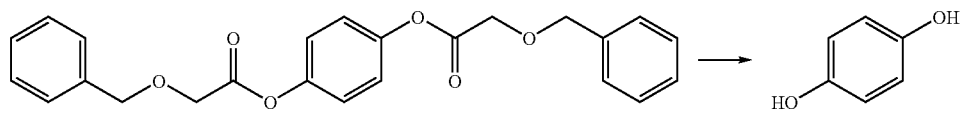

This compound (Example-1) was hydrolyzed to the starting material in 26.5 hours under the conditions described.

Example-45

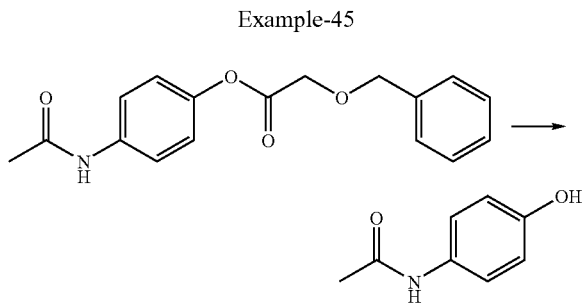

This compound (Example-3) was hydrolyzed to the starting material in 1.5 hours under the conditions described.

Example-46

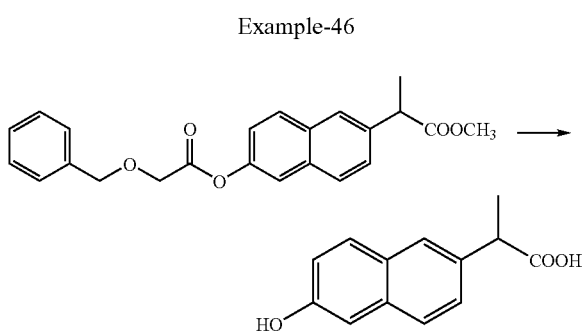

This compound (Example-38) was hydrolyzed to the starting material in 2 hours under the conditions described.

Example-47

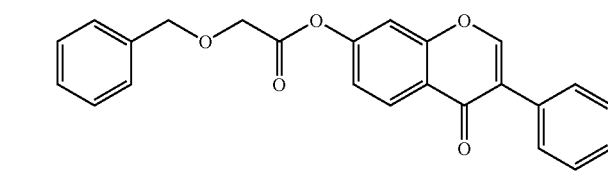

This compound (Example-42) was hydrolyzed to the starting material in 36 hours under the conditions described.

Example-48

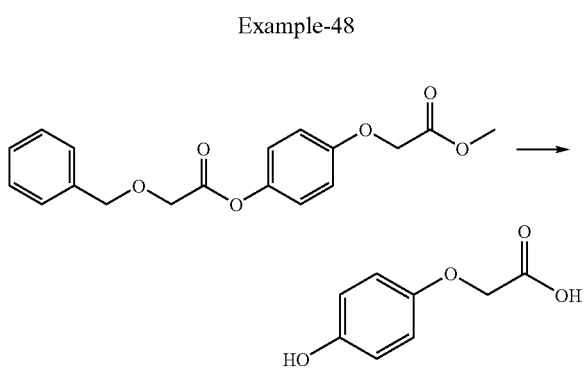

This compound (Example-40) was hydrolyzed to the starting material in 2 hours under the conditions described.

Example-49

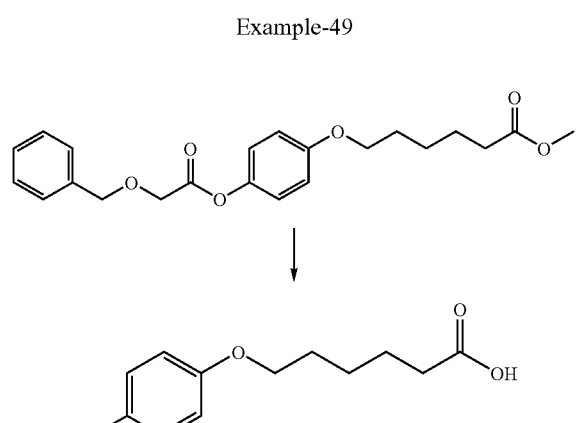

This compound (Example-19) was hydrolyzed to the starting material in 7 hours under the conditions described.

These examples indicate that the polymers derived from the functionalized phenolics should hydrolyze. Therefore, using the functionalized phenolics, one can develop polymers with controlled hydrolysis profiles.

Functionalized Drugs and Bioactive Molecules

Drugs containing OH, NH2, and COOH groups can be functionalized and the resulting functionalized drugs can be reacted to form dimer drugs and oligomeric drugs and/or polymeric drugs with controllable degradation profiles, releasing the active component over desired time range. Some of the examples are illustrated below:

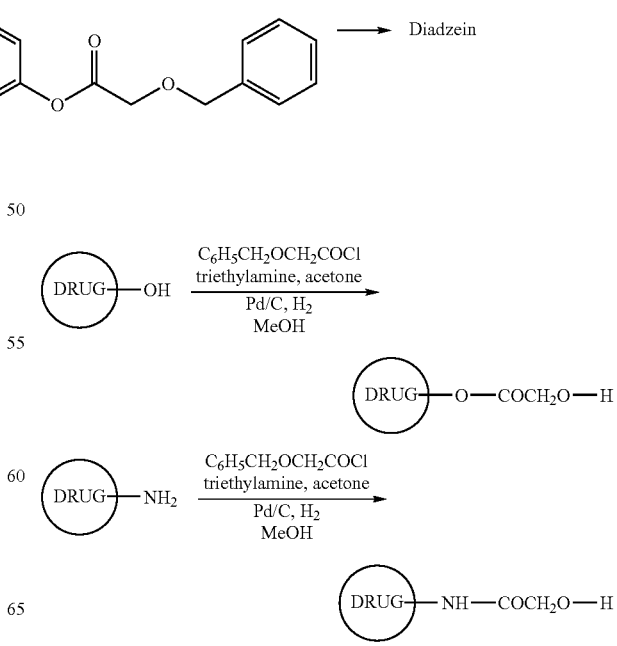

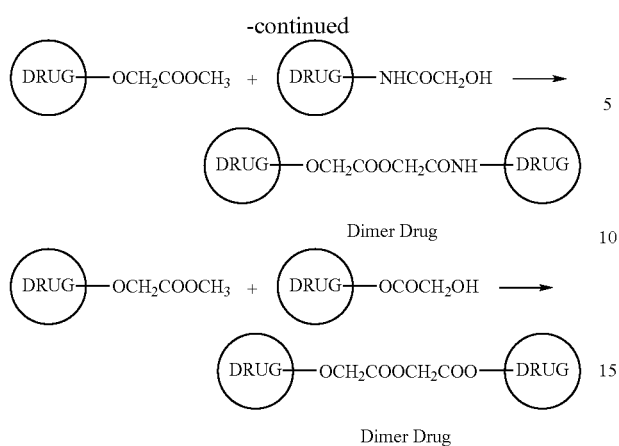

Dimer Drug

Dimer Drug

When the drugs contain difunctional active groups, oligomeric and/or polymeric drugs can be prepared.

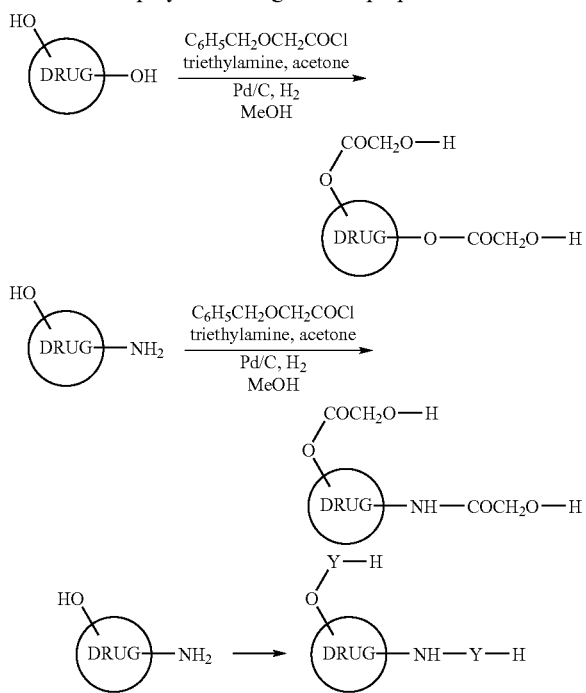

Functionalized Amino Acid-Containing Phenolics

Species of phenolic compounds containing one or more amino acid moieties is also embodied in this invention. Some examples of these amino acids are tyrosine, 3-aminotyrosine, 3-chlorotyrosine, 3,5-dibromotyrosine, 3,5-diiodotyrosine, homotyrosine, 3-Iododtyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, 1,2,3,4-tetrahydroxyisoquinoline-7-hydroxy-3-carboxylic acid, thyronine, 3,4-dihydroxyphenylalanine, 4-hydroxyphenylglycine, amino salicylic acids. This list of phenol containing amino acids is provided for instruction and is not meant to be all-inclusive. One skilled in the art will readily see that the invention can be extended to other phenolic amino acids as well.

In a best mode, a phenol containing an amino acid, such as tyrosine, is functionalized to form a reactive compound, which can be polymerized to form an absorbable polymer with a specific absorption profile.

Some of the possible functionalized tyrosine molecules are listed below:

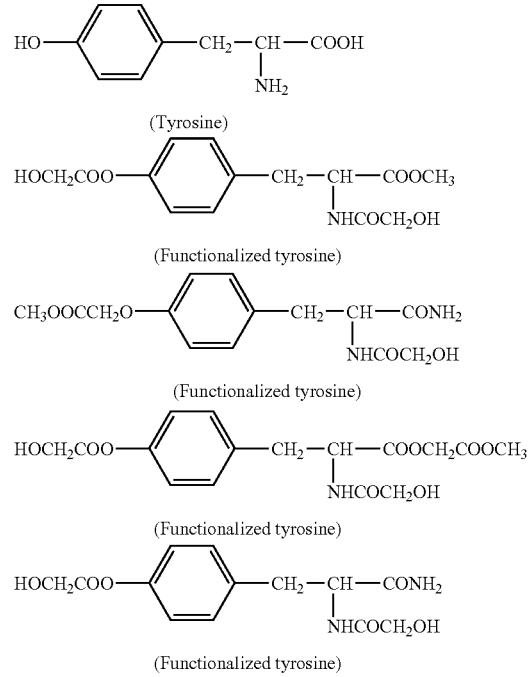

Similarly, each phenol containing amino acids can be functionalized to form reactive monomers. The polymers derived from these monomers have absorption profiles that are controllable.

These polymers can be further polymerized with lactone monomers, such as glycolide, lactide, caprolactone, trimethylene carbonate and/or p-dioxanone, and the resulting absorbable polymers have potential applications, including biomedical applications, such as medical devices, including implantable devices, and drug delivery.

In another aspect of the invention low molecular weight polymers or oligomers of these amino acid containing phenolics are further reacted to form reactive end groups such as isocyanates, expoxides, and acrylates. Functionalized phenolics behave chemically like diols. They can be reacted with dicarboxylic acids to form polyesters, which are usually hydroxyterminated. These hydroxyterminated oligomers can be further reacted to form isocyanates, epoxides and acrylates. Similarly the functionalized phenolic compounds can be reacted with isocyanates to make urethanes.

Functionalized phenolics with at least two reactive sites are polymerized with the functionalization molecules to form absorbable polymers, including but not limited to polyesters, polyester amides, and polyurethanes by simple polycondensation reactions. The absorption profile will depend upon the functionalization species used. Glycolic acid based polymers hydrolyze faster than p-dioxanone based, where as lactic acid and caprolactone based polymers take much longer to hydrolyze than glycolic acid and p-dioxanone based polymers. The desired time range may be obtained by using a combination of functionalized phenolic compounds, that is, a blend of two or more functionalized compounds made from any two or more of the species glycolide, lactide, dioxanone and polydioxanone combined with one phenolic compound. These polymers can be used in various compositions or can be further polymerized with lactone monomers, such as glycolide, lactide, caprolactone, trimethylene carbonate and p-dioxanone, and the resulting absorbable polymers have potential applications, including biomedical applications such as medical devices, including implantable devices, and drug delivery systems.

Blends of the functionalized phenolic compounds are also readily polymerized to form polymers with controllable rates of degradation.

In another aspect of this invention the polymers made from functionalized phenolic compounds are sterilizable by cobalt-60 radiation, electron beam radiation, and/or ethylene oxide, thus making them suitable for use as medical devices.

Examples of several phenolic compounds and/or classes of compounds that when functionalized are polymerizable are:

A. Isopimpinellin, which when functionalized has the native value of the isopimpinellin enhanced by providing a specific controlled degradation profile or range enabling controlled release of the isopimpinellin. Absorbable polymers derived from functionalized isopimpinellin are suitable for many applications, including biomedical applications, such as stent coatings. Absorbable functionalized polycoumarins can be prepared with controlled degradation profiles.

B. Isoflavones (flavovoids) which when functionalized have the native value of the isoflavones enhanced by providing specific controlled degradation profiles or ranges enabling controlled release of the isoflavones. Absorbable polymers derived from the functionalized flavonoids with controlled degradation profiles are suitable for many applications for the targeted delivery of active phenolic component, including biomedical applications, drugs, nutrition supplements, nutriceuticals, drug delivery, cosmetic applications, flavors, and coatings.

C. Resveratrol which when functionalized has the native value of the resveratrol enhanced by providing a specific controlled degradation profile or range enabling controlled release of the resveratrol. Absorbable polymers derived from the functionalized resveratrol are suitable for many applications, including biomedical applications, such as stent coating and drug delivery.

D. Bioflavonoids which when functionalized has the native value of the bioflavonoids enhanced by providing a specific controlled degradation profile or range enabling controlled release of the bioflavonoids. Absorbable polymers derived from the functionalized bioflavonoids are suitable for applications including biomedical applications, such as stents, stent coatings, and drug delivery.

E. Capsaicin which when functionalized has the native value of the capsaicin enhanced by providing a specific controlled degradation profile or range enabling controlled release of the capsaicin. Absorbable polymers derived from the functionalized capsaicin are suitable for applications, including biomedical applications, such as stent coatings, and drug delivery.

F. Sinapinic acid which when functionalized has the native value of the sinapinic acid enhanced as, for example, an anti-inflammatory drug and antimicrobial agent by providing a specific controlled degradation profile or range enabling the controlled release of the sinapinic acid. Absorbable polymers derived from the functionalized sinapinic acids are suitable for applications, including biomedical applications, drugs, nutrition supplements, nutriceuticals, drug delivery, cosmetics, flavors, and coatings.

G. Naproxen, paracetamol, and acetylsalicylic acid which when functionalized have the native value of these drugs enhanced, for example, as an anti-inflammatory by providing a specific controlled degradation profile or range enabling the controlled release of the drug. Absorbable polymers derived from the functionalized drugs are suitable for applications, including biomedical applications, and drug delivery.

Biodegradable Chewing Gums

After conventional chewing gum is chewed, the gum cud that remains that must be discarded. Unfortunately, conventional gum cuds can easily adhere to any dry surface, such as wood, concrete, paper and cloth. When gum cuds are improperly discarded, they can be difficult to remove from such surfaces, causing some environmental concerns. Recently, there has been a move to develop a chewing gum which is either ingestible or that creates a gum cud that is easily removable and degradable. Therefore, one of the objects of this invention is to develop hydrolyzable and flexible elastomers that can be used in conventional and specialized biomedical chewing gum. Some of the compositions of this invention can provide improved chewing gum and gum bases. The improved chewing gum and gum bases are biodegradable and do not cause environmental concerns if improperly discarded.

Bioactive Formulations

In other aspects of this invention some functionalized phenolics of this invention are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, *The Pharmaceutical Basis of Therapeutics*, current edition.

Compounds of the present invention have potent antioxidant activity and increased acidity of their phenolic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

The invention claimed is:

1. A polymer comprising a unit having the formula:

AR—O—Y—R'

AR—O— is a biologically active phenolic moiety selected from the group consisting of isopimpinellin, isoflavones, resveratrol, and bioflavonoids substituted with a functional group selected from the group consisting of alkoxy, benzyloxy, aldehyde, halogen, carboxylic acid, —$NO_2$, —$NH_2$, —$NHCOCH_3$, —NH—Y—R', and a combination thereof, Y represents a member selected from the group consisting of:
    —$COCH_2O$— (glycolic ester moiety)
    —$COCH(CH_3)O$— (lactic ester moiety)
    —$COCH_2OCH_2CH_2O$— (dioxanone ester moiety)
    —$COCH_2CH_2CH_2CH_2CH_2O$— (caprolactone ester moiety)
    —$CO(CH_2)_mO$— where m is an integer between 2-4 and 6-24 inclusive,
    —$COCH_2$—O—$(CH_2CH_2O)_n$— where n is an integer between 2 and 24, inclusive;

and the carbonyl end of Y is attached to the O— of said biologically active phenolic moiety to form an ester linkage; and R' is either hydrogen or a benzyl or an alkyl group, the alkyl group being either straight-chained or branched.

2. The polymer of claim 1, wherein said biologically active phenolic moiety comprises an active site for polymerization selected from the group consisting of a hydroxyl group, a carboxylic acid group, and an amine group.

3. The polymer of claim 2, wherein said active site for polymerization is a hydroxyl group.

4. The polymer of claim 2, wherein said active site for polymerization is an amine group.

5. The polymer of claim 2, wherein said active site for polymerization is a carboxylic acid group.

6. A biologically active composition comprising an effective amount of at least one polymer of claim 1 and a pharmaceutically acceptable excipient, wherein said composition is in a form suitable for oral, enteral, parenteral, topical, transdermal, ocular, vitreal, rectal, nasal, pulmonary, or vaginal administration.

7. An article comprising a metal or polymeric substrate and having thereon a coating, wherein said coating comprises at least one polymer according to claim 1.

8. The article of claim 7, wherein said article is an implantable bio-medical device.

9. An implantable biomedical device comprising the polymer according to claim 1.

10. A cosmetic composition comprising an effective amount of at least one polymer of claim 1 and one or more cosmetic ingredients.

11. A pharmaceutical composition comprising an effective amount of at least one polymer of claim 1 and a pharmaceutically acceptable excipient.

12. A biodegradable chewing gum composition comprising at least one polymer of claim 1.

13. An antioxidant composition comprising an effective amount of at least one polymer of claim 1.

14. The composition comprising at least one polymer according to claim 1, which is further polymerized with at least one lactone monomer selected from the group consisting of glycolide, lactide, p-dioxanone, trimethylene carbonate and caprolactone.

15. An implantable biomedical device comprising the composition according to claim 14.

16. A biodegradable chewing gum composition comprising at least one polymer of claim 14.

17. An antioxidant composition comprising an effective amount of the polymer of claim 14.

18. The polymer of claim 1, wherein said biologically active phenolic moiety is an isoflavone or an isopimpinellin or a combination thereof.

19. The polymer according to claim 18, wherein the isoflavone is selected from the group consisting of: biochanin A, daidzein, formononetin, genistein, glycitein, orobol, pratensein, prunetin, and santal, and glucosides or β-glycosides thereof or a combination thereof.

20. The polymer of claim 19, wherein the isoflavone is selected from the group consisting of daidzein, equol, and gycitein or a combination thereof.

21. The polymer of claim 1, wherein said phenolic moiety is resveratrol.

22. A method for delivering a therapeutic polymer to a patient in need of antioxidant therapy comprising administering to the patient an antioxidant composition comprising an effective amount of the polymer of claim 2.

* * * * *